United States Patent
Forsell

(10) Patent No.: US 9,675,460 B2
(45) Date of Patent: Jun. 13, 2017

(54) IMPLANTABLE MEDICAL DEVICE FOR LUBRICATING AN ARTIFICIAL CONTACTING SURFACE

(76) Inventor: Peter Forsell, Bouveret (CH)

(\*) Notice: Subject to any disclaimer, the term of this patent is extended or adjusted under 35 U.S.C. 154(b) by 0 days.

(21) Appl. No.: 13/383,270

(22) PCT Filed: Jul. 12, 2010

(86) PCT No.: PCT/SE2010/050830
§ 371 (c)(1),
(2), (4) Date: Jan. 10, 2012

(87) PCT Pub. No.: WO2011/005211
PCT Pub. Date: Jan. 13, 2011

(65) Prior Publication Data
US 2012/0116310 A1 May 10, 2012

Related U.S. Application Data

(60) Provisional application No. 61/229,738, filed on Jul. 30, 2009, provisional application No. 61/229,739, (Continued)

(30) Foreign Application Priority Data

Jul. 10, 2009 (SE) ..................................... 0900957
Jul. 10, 2009 (SE) ..................................... 0900958
(Continued)

(51) Int. Cl.
*A61F 2/34* (2006.01)
*A61F 2/30* (2006.01)
(Continued)

(52) U.S. Cl.
CPC ...... *A61F 2/30756* (2013.01); *A61B 17/1666* (2013.01); *A61F 2/30* (2013.01);
(Continued)

(58) Field of Classification Search
CPC .............. A61F 2002/30673; A61F 2/34; A61F 2002/30675; A61F 2002/3068; A61F 2/3603; A61M 5/14276
(Continued)

(56) References Cited

U.S. PATENT DOCUMENTS 4,718,893 A * 1/1988 Dorman et al. ................. 604/67
5,120,312 A * 6/1992 Wigness et al. ............... 604/175
(Continued)

FOREIGN PATENT DOCUMENTS

WO   WO95/01139    * 1/1995 ............... A61F 2/32
WO   WO 95/01139      1/1995
(Continued)

OTHER PUBLICATIONS

International Search Report for PCT/SE2010/050830, mailed Oct. 13, 2010.

*Primary Examiner* — Theodore Stigell
*Assistant Examiner* — Benjamin Koo

(57) ABSTRACT

An implantable medical device for implantation in a mammal joint having at least two contacting surfaces is provided. The medical device comprises; an artificial contacting surface adapted to replace at least the surface of at least one of the mammal's joint contacting surfaces, wherein the artificial contacting surface is adapted to be lubricated, when implanted in said joint. Furthermore the medical device comprises at least one inlet adapted to receive a lubricating fluid from a reservoir, at least one channel at least partly integrated in the artificial contacting surface in connection with the at least one inlet for distributing the lubricating fluid to the surface of the artificial contacting surface. The medical device could be adapted to be operable by an operation device to receive the distributed lubricated fluid from a reservoir.

14 Claims, 28 Drawing Sheets

Related U.S. Application Data filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(30) Foreign Application Priority Data

| Jul. 10, 2009 | (SE) | 0900959 |
|---|---|---|
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |
| Jul. 10, 2009 | (SE) | 0900968 |
| Jul. 10, 2009 | (SE) | 0900969 |
| Jul. 10, 2009 | (SE) | 0900970 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900976 |
| Jul. 10, 2009 | (SE) | 0900978 |
| Jul. 10, 2009 | (SE) | 0900981 |

(51) Int. Cl.

| A61F 2/32 | (2006.01) |
|---|---|
| A61B 17/16 | (2006.01) |
| A61B 17/56 | (2006.01) |
| A61B 17/74 | (2006.01) |
| A61B 17/86 | (2006.01) |
| A61F 2/36 | (2006.01) |
| A61F 2/46 | (2006.01) |
| A61F 2/48 | (2006.01) |
| A61M 5/142 | (2006.01) |
| A61B 17/88 | (2006.01) |
| A61B 18/04 | (2006.01) |
| A61F 2/38 | (2006.01) |
| A61L 27/16 | (2006.01) |
| A61L 31/04 | (2006.01) |
| A61L 31/14 | (2006.01) |

(52) U.S. Cl.
CPC ............ *A61F 2/30721* (2013.01); *A61F 2/32* (2013.01); *A61F 2/34* (2013.01); *A61B 17/1604* (2013.01); *A61B 17/1637* (2013.01); *A61B 17/1664* (2013.01); *A61B 17/1668* (2013.01); *A61B 17/562* (2013.01); *A61B 17/74* (2013.01); *A61B 17/86* (2013.01); *A61B 17/8805* (2013.01); *A61B 18/04* (2013.01); *A61B 2018/046* (2013.01); *A61F 2/30942* (2013.01); *A61F 2/36* (2013.01); *A61F 2/3601* (2013.01); *A61F 2/3603* (2013.01); *A61F 2/389* (2013.01); *A61F 2/3859* (2013.01); *A61F 2/46* (2013.01); *A61F 2/4618* (2013.01); *A61F 2002/30065* (2013.01); *A61F 2002/3067* (2013.01); *A61F 2002/30471* (2013.01); *A61F 2002/30507* (2013.01); *A61F 2002/30558* (2013.01); *A61F 2002/30563* (2013.01); *A61F 2002/30565* (2013.01); *A61F 2002/30579* (2013.01); *A61F 2002/30583* (2013.01); *A61F 2002/30668* (2013.01); *A61F 2002/30672* (2013.01); *A61F 2002/30673* (2013.01); *A61F 2002/30675* (2013.01); *A61F 2002/30754* (2013.01); *A61F 2002/30757* (2013.01); *A61F 2002/30759* (2013.01); *A61F 2002/30878* (2013.01); *A61F 2002/30886* (2013.01); *A61F 2002/3241* (2013.01); *A61F 2002/3483* (2013.01); *A61F 2002/3496* (2013.01); *A61F 2002/3615* (2013.01); *A61F 2002/3631* (2013.01); *A61F 2002/4631* (2013.01); *A61F 2002/4635* (2013.01); *A61F 2002/4655* (2013.01); *A61F 2002/4677* (2013.01); *A61F 2002/482* (2013.01); *A61F 2002/485* (2013.01); *A61F 2250/00* (2013.01); *A61L 27/16* (2013.01); *A61L 31/042* (2013.01); *A61L 31/044* (2013.01); *A61L 31/046* (2013.01); *A61L 31/148* (2013.01); *A61L 2300/406* (2013.01); *A61L 2400/06* (2013.01); *A61L 2430/24* (2013.01); *A61M 5/14276* (2013.01); *A61M 2005/14284* (2013.01)

(58) Field of Classification Search
USPC ........ 604/151, 891.1, 502; 623/22.21–23.38, 623/22.13
See application file for complete search history.

(56) References Cited

U.S. PATENT DOCUMENTS

| 5,378,228 | A | * | 1/1995 | Schmalzried et al. | 604/8 |
|---|---|---|---|---|---|
| 5,616,121 | A | * | 4/1997 | McKay | 604/35 |
| 5,641,323 | A | * | 6/1997 | Caldarise | 623/22.18 |
| 5,681,289 | A | * | 10/1997 | Wilcox et al. | 604/175 |
| 6,764,472 | B1 | * | 7/2004 | Burke et al. | 604/288.04 |
| 7,144,427 | B2 | * | 12/2006 | Southworth | 623/22.13 |
| 2003/0060891 | A1 | * | 3/2003 | Shah | 623/22.13 |
| 2003/0204181 | A1 | * | 10/2003 | Starkebaum | A61F 5/0026 604/891.1 |
| 2007/0088442 | A1 | | 4/2007 | Shelton | |
| 2007/0233019 | A1 | * | 10/2007 | Forsell | 604/288.03 |
| 2010/0042213 | A1 | * | 2/2010 | Nebosky et al. | 623/16.11 |

FOREIGN PATENT DOCUMENTS

| WO | 03049650 A1 | 6/2003 |
|---|---|---|
| WO | WO 2009/048373 | 4/2009 |

* cited by examiner

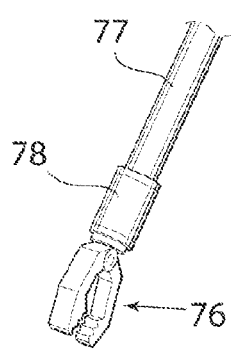
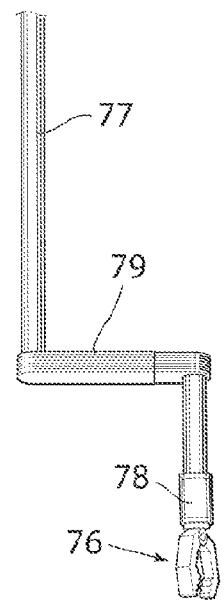
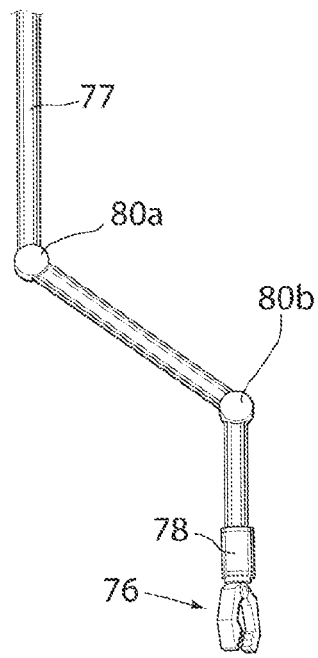
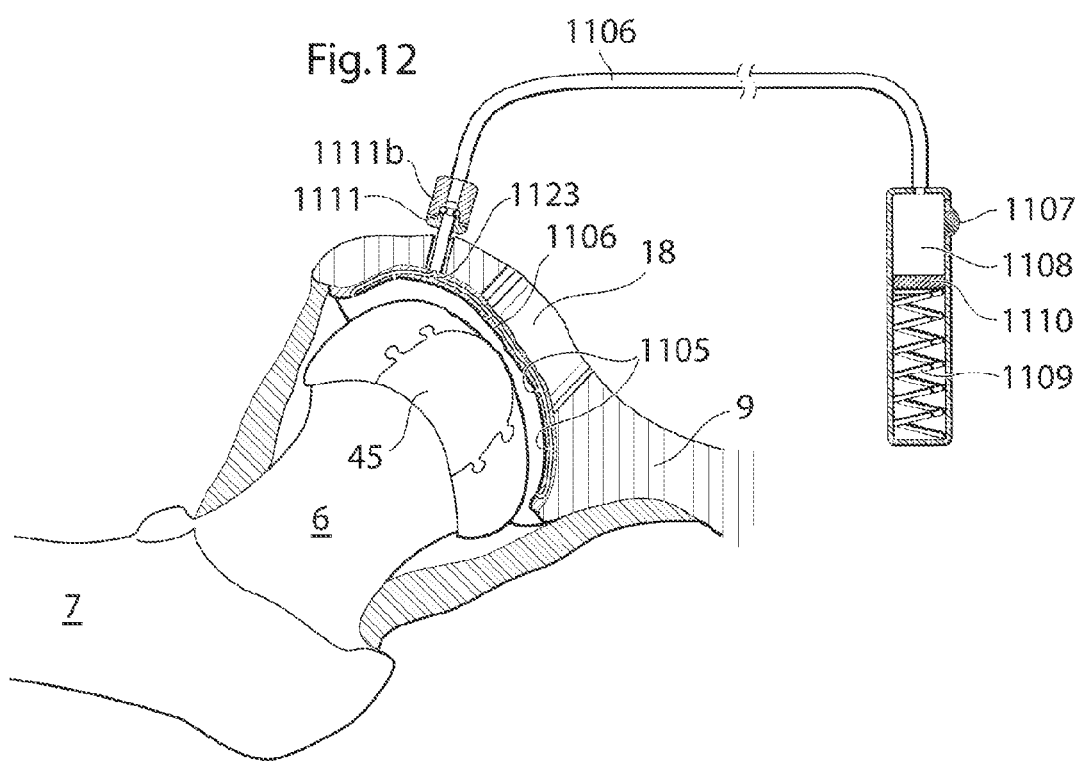

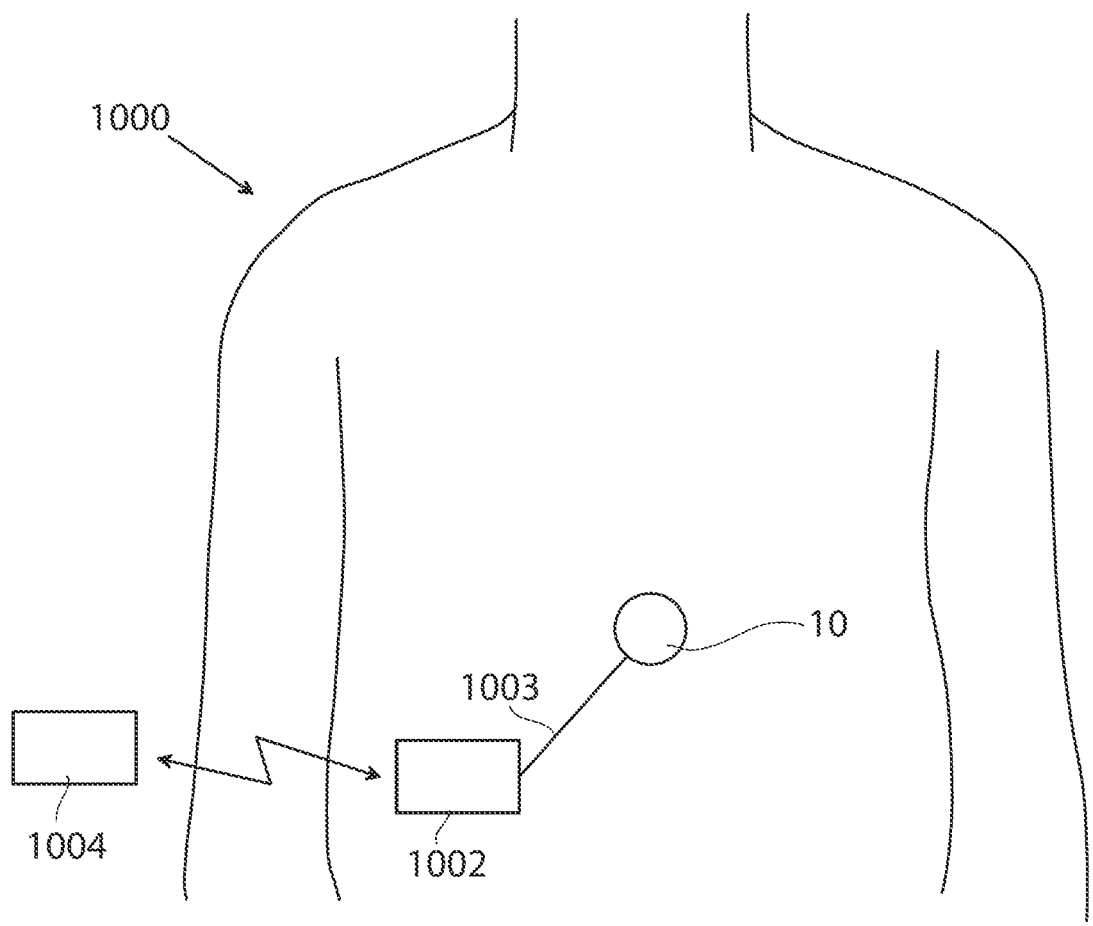

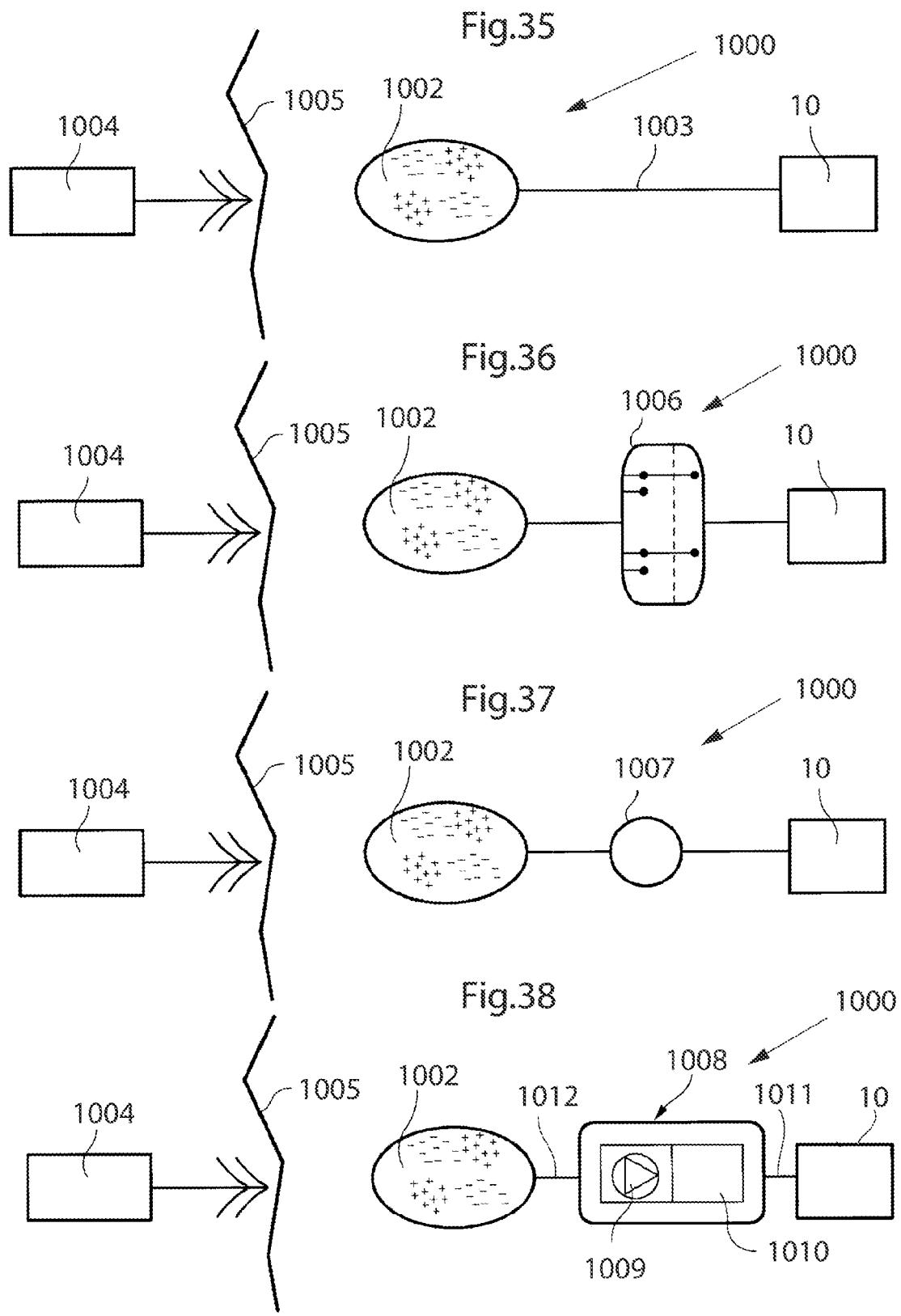

IMPLANTABLE MEDICAL DEVICE FOR LUBRICATING AN ARTIFICIAL CONTACTING SURFACE

This application is the U.S. national phase of International Application No. PCT/SE2010/050830, filed 12 Jul. 2010, which designated the U.S. and claims the benefit of U.S. Provisional Nos. 61/229,755, filed 30 Jul. 2009; 61/229,738 filed 30 Jul. 2009, 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

TECHNICAL FIELD

The present invention relates generally to medical implants.

BACKGROUND

The lubricating fluid (synovial fluid) reduces friction between the articular cartilage and other tissues in a joint and lubricates and cushions the bone and tissue components of the joint during movement. If the lubricating fluid is negatively affected and/or the joint articular cartilage usually covering the bone of the joint is damaged, in most cases due to older age and/or continuing extensive or abnormal strain on human or mammal joints (e.g. knee joint, hip joint), this can result in a degenerative joint disease (also known as osteoarthritis) characterized by a painful inflammation of the joint. Upon pathological reduction and change of composition of the lubricating fluid within the joint space, which consists of the articulating surfaces of the adjacent bones with the joint being stabilized and encompassed by the joint capsule and the synovial membrane, the lubricating fluid can no longer perform its usual task, i.e. lubrication of joint areas and shock absorption, together with the articular cartilage.

If the articular cartilage is severely damaged due to osteoarthritis or the like and/or the synovial fluid is reduced or altered in its composition reducing its potential to lower friction within the joint, the articulating surfaces are subjected to high friction and increased wear causing a painful inflammation of the joint. This can result in serious restraints of movement, especially in walking and standing, which further augment degenerative processes of the joint. Degenerative joint disease is highly prevalent in the western world, with this disease being one of the leading causes for chronic disability in Europe and the US.

Patients with osteoarthritis require a regular long term treatment by which lubricating fluid is introduced into the affected joint, which, on the one hand, re-stores the physiological functionality of the damaged joint as far as possible and, on the other hand, involves as little extra stress as possible—both physical and psychological—for the patient.

A known standard therapy is periodical extracorporeal injection of synthetic lubricating fluid into the joint space by a syringe in order to substitute the absent physiological lubricating fluid. In such conventional treatment it is inconvenient for the patient to deliver the lubricating fluid at regular time intervals through the skin and the joint capsule into the joint by way of a syringe. Also, this may cause injuries to the skin and the joint capsule, which increases the risk of severe infections of the delicate joint tissues. Therefor, an injection may not be performed more often than every 6 months.

Artificial joints have been an important part restoring the functionality of the natural joints of patients suffering from joint osteoarthritis and fractured and damaged joints. Among the most successful material combinations is the ceramic and polymer combination called the Charnley type joint. This prosthesis type however, has a limited life span of 15-20 years due to wear of the polymer component. The particles created from the polymer wear triggers a macrophage reaction which has been found affects the fixation of the prosthesis in the femoral bone and in worst cases makes the prosthesis come loose. Loosening of prosthesis is the number one reason for having to redo hip joint surgery. Since the polymer material of the prosthetic Acetabular cup is relatively soft, the material need to be of considerable thickness for being stiff enough, for enabling fixation of the cup and for resisting the wear from the contact with the prosthetic caput femur. The use of harder materials in the Acetabular cup have the disadvantages of creating sounds when walking which propagates out of the body, furthermore harder material do not create the desired elastic properties which is needed for reduce strains placed on the fixations of the prosthetic parts against the natural bone tissue.

SUMMARY

Please note that any embodiment or part of embodiment as well as any method or part of method could be combined in any way. All examples herein should be seen as part of the general description and therefore possible to combine in any way in general terms.

Please note that the description in general should be seen as describing both of an apparatus and a method.

The various aforementioned features of the embodiments may be combined in any way if such combination is not clearly contradictory.

An implantable medical device for implantation in a mammal joint having at least two contacting surfaces is provided. The implantable medical device comprising an artificial concave acetabulum contacting surface adapted to replace the surface of the acetabulum contacting surface. The artificial concave acetabulum contacting surface is adapted to be lubricated, when implanted in said joint, At least one inlet is adapted to receive a lubricating fluid from a reservoir, and at least one channel at least partly integrated in said artificial concave acetabulum contacting surface, wherein the channel is in fluid connection with said at least one inlet for distributing said lubricating fluid to the surface of said artificial concave contacting surface. The medical device could be adapted to be operable by an operation device to receive the distributed lubricating fluid from a reservoir. The possibility to inject a lubricating fluid intermittently or when needed reduces the friction in the joint and enables an optimal level of lubrication in the joint.

According to one embodiment of the implantable medical device, the at least one channel could be adapted to distribute the lubricating fluid to the surface of the artificial contacting surface on two or more portions of the artificial contacting surface for lubricating the artificial contacting surface. The distribution in more than one portion could enable a more even distribution of the lubricating fluid.

According to another embodiment the medical device further comprises a reservoir adapted to hold the lubricating fluid. The reservoir could be an implantable reservoir placed in a cavity of the body, subcutaneously or in connection with bone.

The implantable medical device could further comprise an operation device adapted to transport a lubricating fluid from a reservoir to the artificial contacting surface for lubricating the artificial contacting surface.

According to one embodiment a reservoir could be adapted to hold the lubricating fluid and the operation device according to any of the embodiments herein could be adapted to transport the lubricating fluid from the reservoir to the artificial contacting surface for lubricating the artificial contacting surface. The operation device could be powered and could comprise a pump adapted to pump fluid from the reservoir to the artificial contacting surface for lubricating the artificial contacting surface.

The operation device, according to any of the embodiments herein could comprise a reservoir, pre-loaded with pressurized lubricating fluid.

According to another embodiment, the implantable medical device could further comprise an implantable injection port adapted to allow, by injection into the injection port, to pre-load the reservoir with pressurized lubricating fluid.

The implantable medical device could, according to one embodiment, further comprise a valve adapted to close the connection between the reservoir and the artificial contacting surface. The reservoir could be adapted to be placed in a unit separate from the artificial contacting surface and adapted to be connected to the artificial contacting surface with a conduit. The reservoir could comprise a moveable wall portion adapted to move and change the volume of the reservoir, the wall portion could be a powered wall portion which could comprise a motor.

According to another embodiment, the implantable medical device could comprise at least one outlet and at least one further channel at least partly integrated in the artificial contacting surface. The medical device could be adapted to allow circulation of a lubricating fluid; out from the artificial contacting surface through the outlet and in to the artificial contacting surface through the inlet. The circling of the fluid could be performed by means of an operation device adapted to circulate the lubricating fluid. The circling system could comprise a reservoir adapted to add fluid to the circulating lubricating fluid, and/or a filter to clean the circulating lubricating fluid.

The operation device according to any of the embodiments could be adapted to intermittently transport a lubricating fluid to the artificial contacting surface.

The implantable medical device could according to one embodiment comprise a sensor adapted to sense a physical parameter inside the joint, or a pressure or volume of the lubricating fluid, or a functional parameter of the operation device to control the operation device to adjust the flow of lubricating fluid to the artificial contacting surface.

The reservoir according to any of the embodiments could be connected to the reservoir through a conduit. The inlet could comprise a connection part, for connecting the conduit to the medical device. The conduit, according to any of the embodiments could comprise a plurality of portions, which could be adapted to be connected to each other through an inter-connecting part. A first portion of the conduit could be in connection with the medical device, and the second portion of the conduit could be in connection with the reservoir. The conduit could according to one embodiment be adapted to pass through a bone of the body for long-term keeping a passage way open through the bone, allowing the lubricating fluid to reach the artificial contacting surface. According to another embodiment the conduit is adapted to pass through a joint capsule of the body for long-term keeping a passage way open through the joint capsule, allowing the lubricating fluid to reach the artificial contacting surface and according to yet another embodiment the conduit is adapted to pass through the pelvic bone from the opposite said of the acetabulum and into the hip joint.

The implantable medical device could be adapted to be implanted in a hip joint of a patient, in which case the artificial contacting surface of the medical device could be adapted to at least partly replace a contacting surface of the Acetabulum, and/or the Caput femur.

The implantable medical device could according to one embodiment further comprise a second artificial contacting surface. According to one embodiment the first artificial contacting surface comprises a convex shape towards a centre of the hip joint and the second artificial contacting surface comprises a concave shape towards the centre of the hip joint. The first artificial contacting surface is according to this opposite embodiment adapted to be fixated to the pelvic bone of the human patient, and the second artificial contacting surface is adapted to be fixated to the femoral bone of the human patient.

The implantable medical device could be adapted to be introduced into the hip joint through a hole in the pelvic bone, from the abdominal side of the pelvic bone, an operational method which allows the hip joint capsule to be kept intact.

The reservoir could according to one embodiment be adapted to be placed inside, or at least partly inside of a bone of the patient, the bone could for example be the femoral bone, the pelvic bone or the collum femur of the patient.

According to another embodiment, the reservoir could be adapted to be placed subcutaneously or in a cavity in the body, which could be a cavity in a region selected from a group of regions consisting of: the abdominal region, the inguinal region, the pelvic region, and the thigh region.

The implantable medical device could according to one embodiment comprise an injection port for filling of the reservoir. The injection port could comprise a self sealing membrane, which for example could be a Parylene coated silicone membrane. The injection port could be adapted to be implanted subcutaneously, in connection with bone or in a cavity of the body.

The reservoir could be adapted to place the lubricating fluid under pressure. For achieving the pressure the reservoir could be adapted to be spring loaded, comprise a chamber adapted to hold a compressed gas or comprise an elastic wall adapted to create the pressure. According to one embodiment the reservoir comprises a Parylene coated silicone elastic wall.

According to another embodiment, the implantable medical device is adapted to be implanted in a knee joint of a patient. The artificial contacting surface could according to one embodiment be adapted to at least partly replace a contacting surface of the femoral bone, which could be a contacting surface of the Tibia bone and/or the femoral bone.

According to one embodiment the artificial contacting surface is adapted to replace at least one of the medial or lateral part of the contacting surface of tibia of the knee joint and according to another embodiment the implantable medical device is adapted to replace at least one of the medial or lateral part of the contacting surface of the femoral bone of the knee joint. In yet another embodiment the medical device is adapted to replace both the contacting surface of the femoral bone of the knee joint and the contacting surface of the tibia bone of the knee joint.

According to one embodiment the reservoir according to any of the embodiments is adapted to be refilled from outside of the human body, the refilling could be performed through an implantable injection port.

According to one embodiment, the reservoir is adapted to hold a pressure which is possible to increase through injection of a lubricating fluid through the injection port.

The implantable medical device according to any of the embodiments could be adapted to be a part of a system which further could comprise at least one switch implantable in the patient for manually and non-invasively controlling the implantable medical device. The energized system enables an operation device to operate the lubrication performed by the medical device.

The system could according to one embodiment further comprise a hydraulic device having an implantable hydraulic reservoir, which could be hydraulically connected to the implantable medical device. The implantable medical device could be adapted to be non-invasively regulated by manually pressing the hydraulic reservoir.

According to another embodiment, the system could further comprise a wireless remote control for non-invasively controlling the implantable medical device. The wireless remote control could comprise at least one external signal transmitter and/or receiver, further comprising an internal signal receiver and/or transmitter implantable in the patient for receiving signals transmitted by the external signal transmitter or transmitting signals to the external signal receiver. The wireless remote control could further be adapted to transmit at least one wireless control signal for controlling the implantable medical device. The wireless control signal could comprise a frequency, amplitude, or phase modulated signal or a combination thereof. The wireless remote control could further be adapted to transmit an electromagnetic carrier wave signal for carrying the control signal.

According to another embodiment the system could comprise a wireless energy-transmission device for non-invasively energizing the implantable energy consuming components of the implantable medical device with wireless energy. The wireless energy could comprise a wave signal, selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal, gamma radiation signal, an electric field, a magnetic field, a combined electric and magnetic field.

A control signal in the system could comprise an electric field, a magnetic field, a combined electric and magnetic field. The signal could comprise an analogue signal, a digital signal, or a combination of an analogue and digital signal. For powering the energy consuming components of the implantable medical device, the implantable system could comprise an implantable internal energy source. According to another embodiment the system comprises an external energy source for transferring energy in a wireless mode, wherein the internal energy source is chargeable by the energy transferred in the wireless mode.

According to a further embodiment the system could further comprise a sensor or a measuring device sensing or measuring a functional parameter correlated to the transfer of energy for charging the internal energy source, and a feedback device for sending feedback information from inside the patient's body to the outside thereof, the feedback information could be related to the functional parameter sensed by the sensor or measured by the measuring device.

According to yet another embodiment, the system could further comprise a feedback device for sending feedback information from inside the patient's body to the outside thereof, the feedback information being related to at least one of a physical parameter of the patient and a functional parameter related to the implantable medical device.

The system could according to one embodiment further comprise a sensor and/or a measuring device and an implantable internal control unit for controlling the implantable medical device in response to information being related to at least one of a physical parameter of the patient sensed by the sensor or measured by the measuring device and a functional parameter related to the implantable medical device sensed by the sensor or measured by the measuring device. The physical parameter could according to one embodiment be a pressure or a motility movement.

The system could according to one embodiment comprise an external data communicator and an implantable internal data communicator communicating with the external data communicator, the internal communicator feeds data related to the implantable medical device or the patient to the external data communicator and/or the external data communicator feeds data to the internal data communicator.

The system according to any of the embodiments herein, could further comprise a motor or a pump for operating the implantable medical device, or a hydraulic operation device for operating the implantable medical device. The operation device could comprise a servo designed to decrease the force needed for the operation device to operate the implantable medical device instead the operation device acting a longer way, increasing the time for a determined action.

According to one embodiment the system could further comprise an operation device for operating the implantable medical device. The wireless energy could be used in its wireless state to directly power the operation device to create kinetic energy for the operation of the implantable medical device, as the wireless energy is being transmitted by the energy-transmission device. The system could also comprise an energy-transforming device for transforming the wireless energy transmitted by the energy-transmission device from a first form into a second form energy.

The energy-transforming device could be adapted to directly power implantable energy consuming components of the implantable medical device with the second form energy, as the energy-transforming device transforms the first form energy transmitted by the energy-transmission device into the second form energy. The second form energy could comprise at least one of a direct current, pulsating direct current and an alternating current. The energy of the first or second form could comprise at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

For protecting the system or the parts of the system, the system could further comprise an implantable electrical component including at least one voltage level guard and/or at least one constant current guard. A control device could be arranged to control the transmission of wireless energy from the energy-transmission device, and an implantable internal energy receiver for receiving the transmitted wireless energy, the internal energy receiver could be connected to implantable energy consuming components of the implantable medical device for directly or indirectly supplying received energy thereto, the system could further comprise a determination device adapted to determine an energy balance between the energy received by the internal energy receiver and the energy used for the implantable energy consuming components of the implantable medical device, the control device could be adapted to control the transmission of wireless energy from the external energy-transmission device, based on the energy balance determined by the determination device.

The determination device could be adapted to detect a change in the energy balance, the control device could be adapted to control the transmission of wireless energy based on the detected energy balance change. The determination device could in turn be adapted to detect a difference between energy received by the internal energy receiver and energy used for the implantable energy consuming components of the implantable medical device, and the control device could be adapted to control the transmission of wireless energy based on the detected energy difference.

The energy-transmission device could comprise a coil placed externally to the human body, which in turn could further comprise an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power. The electric circuit could be adapted to deliver the electrical pulses to remain unchanged except varying the first and/or second time intervals.

The system could according to one embodiment have an electric circuit having a time constant which is adapted to vary the first and second time intervals only in the range of the first time constant, so that when the lengths of the first and/or second time intervals are varied, the transmitted power over the coil is varied.

The implantable internal energy receiver for receiving wireless energy could comprise an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

The system could also comprise an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils. The system according to claim 98, wherein the energy transmitter regulates the transmitted energy in response to the obtained coupling factor.

In the embodiments in which the system comprises an external second coil, the external second coil could be adapted to be moved in relation to the internal first coil to establish the optimal placement of the second coil, in which the coupling factor is maximized. The external second coil could also be adapted to calibrate the amount of transferred energy to achieve the feedback information in the determination device, before the coupling factor is maximized.

According to a second aspect, a method of implanting the medical device according to any of the embodiments herein is further provided. The method comprises the steps of: creating an opening reaching from outside of the human body into a joint, providing the artificial contacting surface to the joint, fixating the artificial contacting surface to the joint, implanting the reservoir in the human body, and lubricating the artificial contacting surface with use of a lubricating fluid contained in the reservoir.

The step of lubricating the artificial contacting surface with use of a lubricating fluid contained in the reservoir could comprise implanting an operation device adapted to transport the fluid from the reservoir to the artificial contacting surface. According to another embodiment the step of lubricating the artificial contacting surface with use of a lubricating fluid contained in the reservoir comprises providing an energy source for powering the operation device.

According to yet another embodiment the step of lubricating the artificial contacting surface with use of a lubricating fluid contained in the reservoir could comprise powering the operation device using the energy source.

The step of implanting a reservoir in the human body could, according to one embodiment, comprise the step of implanting an operation device being integrated in the reservoir, allowing the step of lubricating the artificial contacting surface with use of a lubricating fluid contained in the reservoir, using the operation device transporting the fluid from the reservoir to the artificial contacting surface.

Implanting the reservoir, according to any of the embodiments could comprise the step of implanting the reservoir at least partially inside of a bone of the patient, which could be the femoral bone of the patient, the tibia bone of the patient and/or the pelvic bone of the patient.

The step of providing the artificial contacting surface could comprise the step of providing the artificial contacting surface from the abdominal side of the pelvic bone.

The step of implanting the reservoir in the human body could comprise the step of implanting the reservoir subcutaneously. Placing the reservoir subcutaneously allows simple access to the reservoir and eliminates the need for a long conduit between an injection port and the reservoir.

The step of implanting the reservoir subcutaneously could comprise the step of implanting the reservoir in at least one of the regions of the patient selected from a group of regions consisting of: the abdominal region, the inguinal region, the pelvic region, the thigh region, and the calf region.

A further step of implanting an injection port for filling of the reservoir could be performed. The implantation of an injection port could comprise the step of implanting the injection port in connection with bone.

According to one embodiment, the medical device comprises an artificial contacting surface adapted to carry weight in a joint of a patient, the artificial contacting surface could comprise at least one channel for transporting a lubricating fluid, the method comprises the steps of: implanting the medical device in a joint of the human patient, implanting a conduit adapted to be connected to the medical device, implanting an operation device for transporting a lubricating fluid inside the conduit, implanting a reservoir adapted to hold a lubricating fluid, and at least postoperatively transporting, by the operation device, the lubricating fluid from the reservoir to the artificial contacting surface in the conduit and further through the channel in the artificial contacting surface, thereby applying the lubricating fluid to the artificial contacting surface.

Please note that any embodiment or part of embodiment as well as any method or part of method could be combined in any way. All examples herein should be seen as part of the general description and therefor possible to combine in any way in general terms.

BRIEF DESCRIPTION OF THE DRAWINGS

The embodiments are now described, by way of example, with reference to the accompanying drawings, in which:

FIG. 11a-c shows a surgical instrument for use in a method of providing a medical device according to any of the embodiments herein.

FIG. 12 shows the hip joint in section when a medical device has been implanted and connected to an implantable reservoir.

FIG. 34 illustrates a system for treating a disease, wherein the system includes an apparatus of the invention implanted in a patient.

FIGS. 35-49 schematically show various embodiments of the system for wirelessly powering the apparatus shown in FIG. 34.

DETAILED DESCRIPTION

Figure 1:
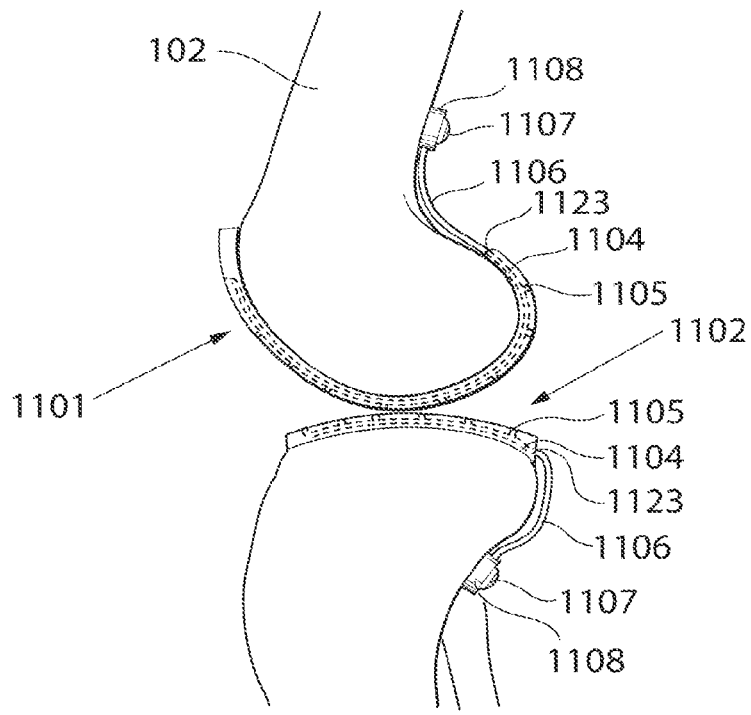
FIG. 1 shows a lateral view of a knee joint when a medical device has been provided.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

Please note that any embodiment or part of embodiment as well as any method or part of method could be combined in any way. All examples herein should be seen as part of the general description and therefor possible to combine in any way in general terms.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical hip device or prosthesis is the position in which the hip joint can perform functional hip movements. The final position is to be understood as a functional position in which the medical device needs no further position change.

Functional knee movements are to be understood as movements of the knee that at least partly correspond to the natural movements of the knee. On some occasions the natural movements of the knee joint might be somewhat limited or altered after knee joint surgery, which makes the functional knee movements of a knee joint with artificial surfaces somewhat different than the functional knee movements of a natural knee joint.

The functional position of an implantable medical knee device or prosthesis is the position in which the knee joint can perform functional knee movements.

Functional knee joint is a knee joint that can perform functional knee movements either with or without an implanted medical device or prosthesis.

Full functional size is to be understood as the size of the medical knee device when said medical device is implanted in the knee joint.

Arthroscopy is to be understood as key hole surgery performed in a joint, since the arthroscopic procedure could be performed in the abdomen of the patient some of the steps of this arthroscopic procedure is more laparoscopic, however for the purpose of this invention the two terms arthroscopy and laparoscopy is used synonymously and for the purpose of this invention the main purpose of these methods are is that they are minimally invasive.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the artificial contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE or UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

FIG. 1 shows a medical device according to an embodiment in which the medical device comprises a first artificial contacting surface 1101 adapted to replace the distal surface of the femoral bone 102, being part of the knee joint. The first artificial contacting surface 1101 could be adapted to replace the surface of the lateral condyle, the medial condyle or both the lateral and medial condyles. The medical device of FIG. 1 further comprises a second artificial contacting surface 1102 being adapted to replace the contacting surface of the tibia bone being the other contacting surface of the knee joint. The implantable medical device comprises an inlet 1123 adapted to receive a lubricating fluid from a reservoir 1108, which according to this embodiment is placed on the rear side of the tibia bone and the rear side of the femoral bone 102, respectively. The reservoir 1108 is according to this embodiment adapted to be refilled by means of an injection port 1107 being placed in fluid contact with the reservoir 1108. The reservoir 1108 supplies the inlet 1123 with a lubricating fluid through a conduit 1106 which supplies a fluid connection between the medical device and the reservoir 1108. The reservoir is according to this embodiment adapted to be placed under pressure through said injection port 1108 comprising chamber for pressurized gas which is further compressed when the reservoir 1108 is being filled through the injection port 1107. The inlet 1123 transports the lubricating fluid to a channel 1105 which is at least partly integrated in said artificial contacting surfaces 1101,1102. According to the embodiment of FIG. 1 the channel 1105 is fully integrated in the medical device. The channel 1105 distributes the lubricating fluid over the artificial contacting surfaces 1101, 1102 and thereby lubricates the artificial contacting surfaces 1101, 1102 and improves the function thereof by reducing the friction. The implantable medical device could just as well be adapted to be implanted in the knee joint of another mammal, such as a horse.

Figure 2:
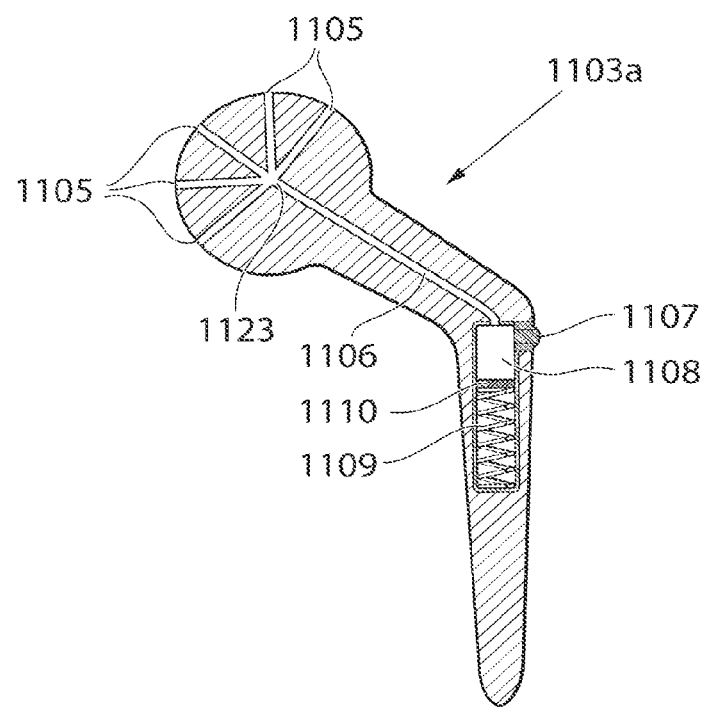
FIG. 2 shows the medical device according to one embodiment, in section.

FIG. 2 shows the implantable medical device according to an embodiment where the medical device is adapted to replace parts of the hip joint. The medical device comprises a plurality of channels 1105 adapted to lubricate the artificial contacting surface of the hip joint by a lubricating fluid being injected to the channel through a conduit 1106 placed centrally in the implantable medical device. The conduit 1106 places the plurality of channels 1105 in fluid connection with a reservoir 1108 which is located in the stem part, adapted for fixation in the femoral bone of a human patient, of said medical device. The conduit 1106 transports lubricating fluid to the inlet 1123 for further distribution to the channels 1105. The reservoir 1108 according to the embodiment of FIG. 2 is spring loaded by a spring 1109 which pushes a movable wall portion in the shape of a piston 1110 for placing said lubricating fluid under pressure. The reservoir 1108 is adapted to be refilled through the injection port 1107, which is placed on the lateral side of the medical device. The injecting of lubricating fluid through the injection port 1107 compresses the spring 1109 which thereby places the lubricating fluid under pressure, which pressure presses the lubricating fluid through the conduit 1106 and to the channels 1105 for lubricating the hip joint of a human patient. The spring loaded reservoir 1108 could be replaced by other types of reservoirs adapted to place a pressure on the lubricating fluid, such as a reservoir 1108 comprising a chamber filled with a pressurized gas which is further pressurized by the injecting of a lubricating fluid through an injection port, it is furthermore conceivable that the reservoir 1108 is an elastic reservoir in which case the elastic properties of the elastic reservoir pressurized the lubricating fluid.

Figure 3:
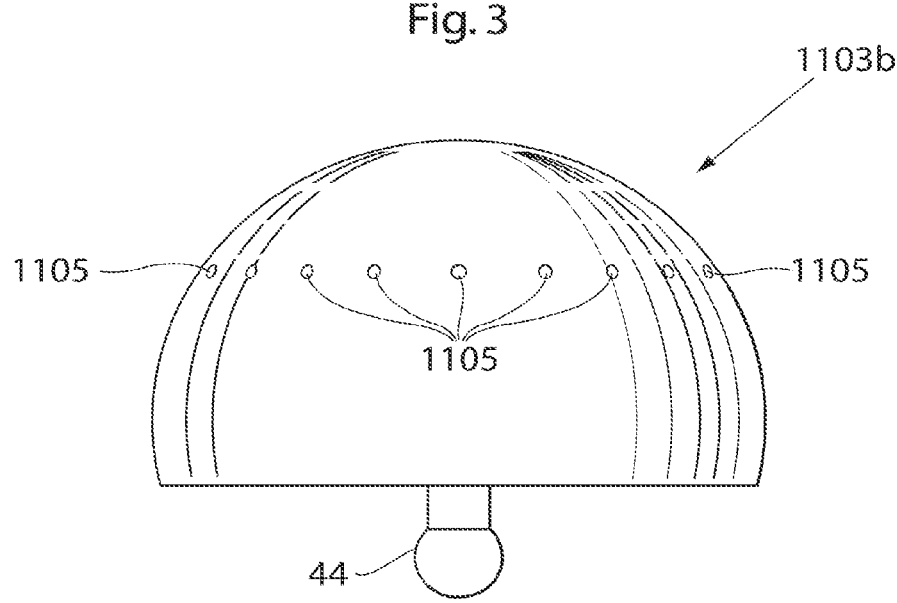
FIG. 3 shows the medical device according to one embodiment comprising an artificial contacting surface.

FIG. 3 shows the medical device according to an embodiment in which the medical device is adapted to replace the contacting surface of the caput femur of the femoral bone of a human patient. The medical device according to this embodiment the artificial contacting surface 1103b of the medical device comprises a plurality of channels adapted to lubricate the hip joint of a human patient with a lubricating fluid. The medical device further comprises a fixating portion 44 for fixating the medical device to the caput femur and/or the collum femur of the femoral bone.

Figure 4:
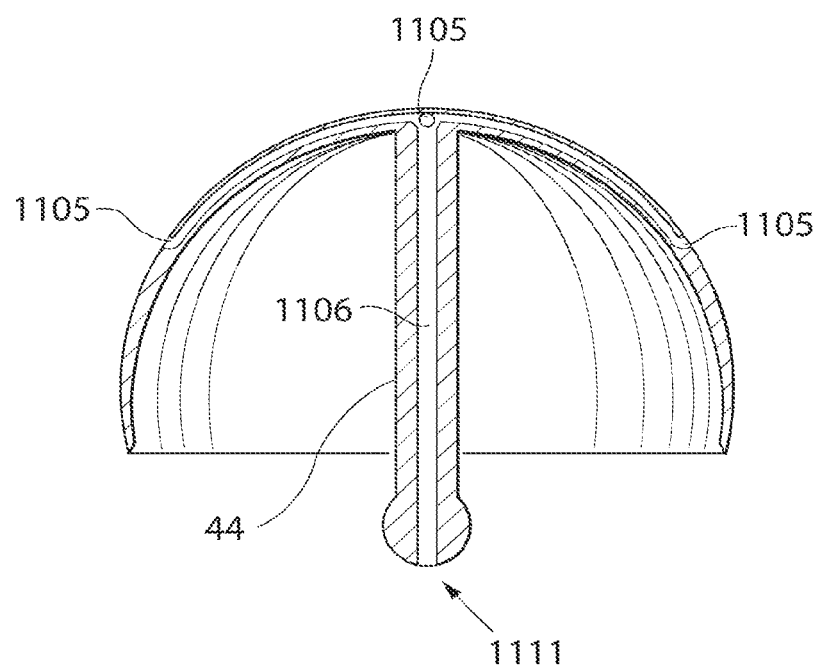
FIG. 4 shows the medical device according to one embodiment comprising an artificial contacting surface, in section.

FIG. 4 shows the medical device according to FIG. 3 in section, showing the medical device comprising a plurality of channels in fluid connection with a reservoir (not shown) through a conduit 1106 placed centrally in the fixating portion 44, the channels 1105 being fully integrated in the medical device. The conduit 1106 transports lubricating fluid to the inlet 1123 for further distribution to the channels 1105. The conduit ends up in a connecting section 1111 which is adapted to connect the conduit to a second conduit or a reservoir, or additional channels.

Figure 5:
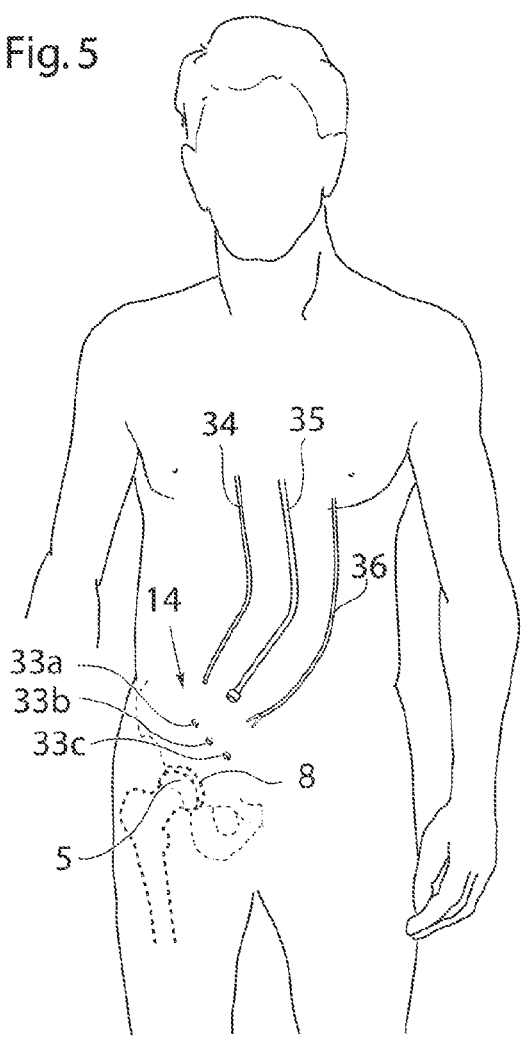
FIG. 5 shows a frontal view of a human patient displaying the hip joint.

FIG. 5 shows a frontal view of the body of a human patient, illustrating a laparoscopic/arthroscopic method of operating the hip joint to provide a medical device according to any of the embodiments herein from the opposite side from acetabulum 8. The hip joint comprises the acetabulum 8 and the caput femur 5. The small incisions 14 in the abdominal wall of the human patient allows the insertion of laparoscopic/arthroscopic trocars 33a,b,c into the body of the patients. Whereafter one or more camera 34, a surgical instrument adapted to create a hole in the pelvic bone 35, or instruments 36 for introducing, placing, connecting, attaching, creating or filling an implantable medical device, can be inserted into the body through said laparoscopic/arthroscopic trocars 33a,b,c.

Figure 6:
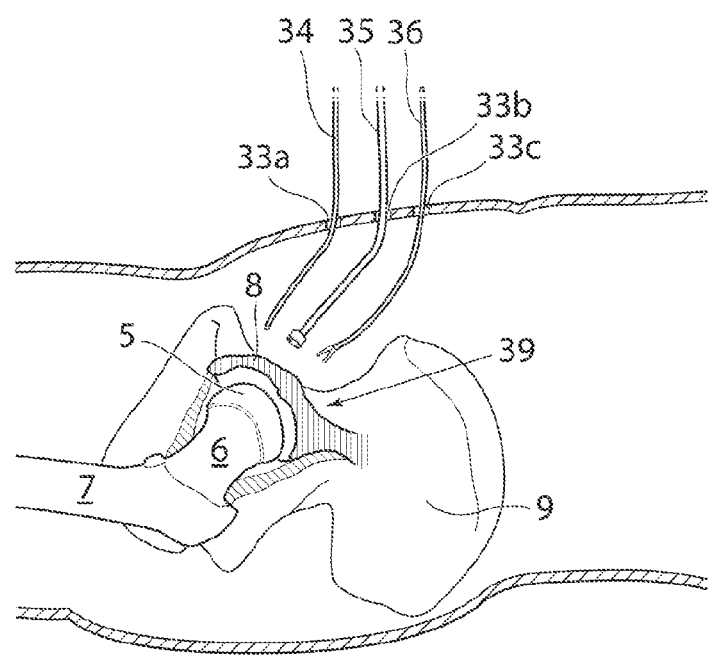
FIG. 6 shows a lateral view of a human patient, in section, when a laparoscopic/arthroscopic procedure is being performed.

FIG. 6 shows a lateral view of the body of a human patient, with the hip joint shown in section. The hip joint comprises a caput femur 5 placed at the very top of collum femur 6 which is the top part of the femur bone 7. The caput femur 5 is in connection with the acetabulum 8 which is a bowl shaped part of the pelvic bone 9. Laparoscopic/arthroscopic trocars 33a,b,c is being used to reach the hip joint 39 with one or more camera 34, a surgical instrument 35 adapted to create a hole in the pelvic bone 9, or instruments 36 for introducing, placing, connecting, attaching, creating or filling an implantable medical device.

Figure 7:
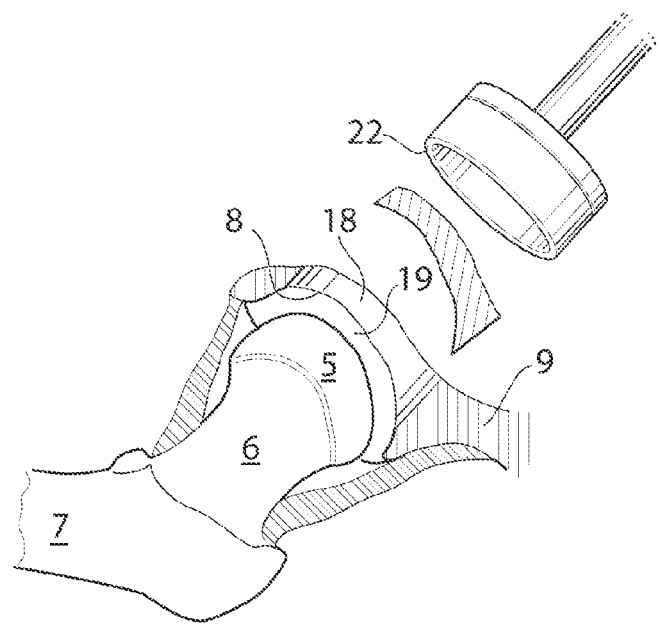
FIG. 7 shows the hip joint in section when a hole in the pelvic bone is being created.

FIG. 7 shows the creation of a hole 18 in the pelvic bone 9, after the pelvic bone 9 has been dissected. The hole 18 is created from the abdominal side of the pelvic bone 9 through repetitive or continuous movement of a hole creating device 22 placed into the human patient from the abdominal side of the pelvic bone 9. The hole 18 passes through the pelvic bone 9 from the opposite side from acetabulum 8 and into the hip joint 19. According to a first embodiment the hole 18 is large which allows an implantable medical device to pass through the hole 18 in its full functional size.

Figure 8A:
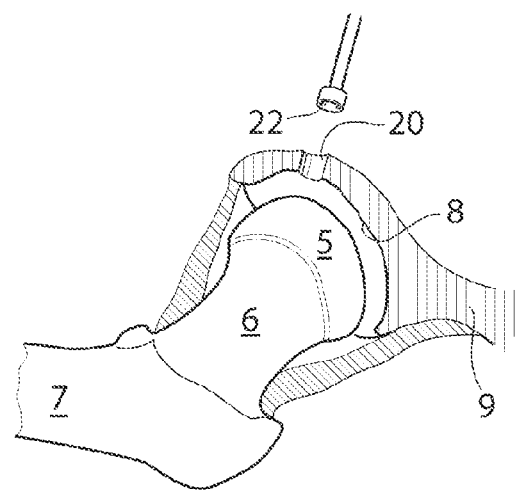
FIG. 8a shows the hip joint in section when a small hole in the pelvic bone is being created.

FIG. 8a shows a second embodiment in which the hole 20 created in a surgical or laparoscopic/arthroscopic method is much smaller as shown in FIG. 8a allowing the hole creating device 22 creating the hole 20 to be smaller, and thus also the incision and dissection performed in the human body.

Figure 8B:
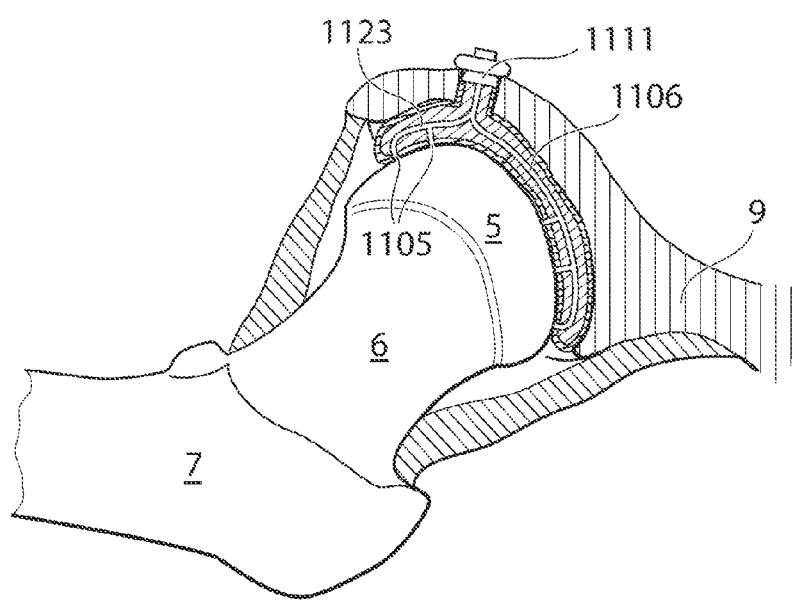
FIG. 8b shows the hip joint in section when a medical device has been provided through a hole in the pelvic bone.

FIG. 8b shows the hip joint in section when a medical device has been provided between the caput femur 5 and the acetabulum. The medical device according to this embodiment comprises multiple channels 1105 connected to a conduit 1106 which in turn is connected to a connecting portion placed in the hole in the pelvic bone 9. The conduit 1106 transports lubricating fluid to the inlet 1123 for further distribution to the channels 1105. For insertion through a hole 18 in the pelvic bone 9 being smaller than the medical device the medical device could be rolled or compressed, or according to another embodiment, molded in place either in a mould adapted to be resorbed by the human body, melt or serve as the surface of the medical device. The medical device could be adapted to be fixated using adhesive or a mechanical fixating element.

Figure 9A:
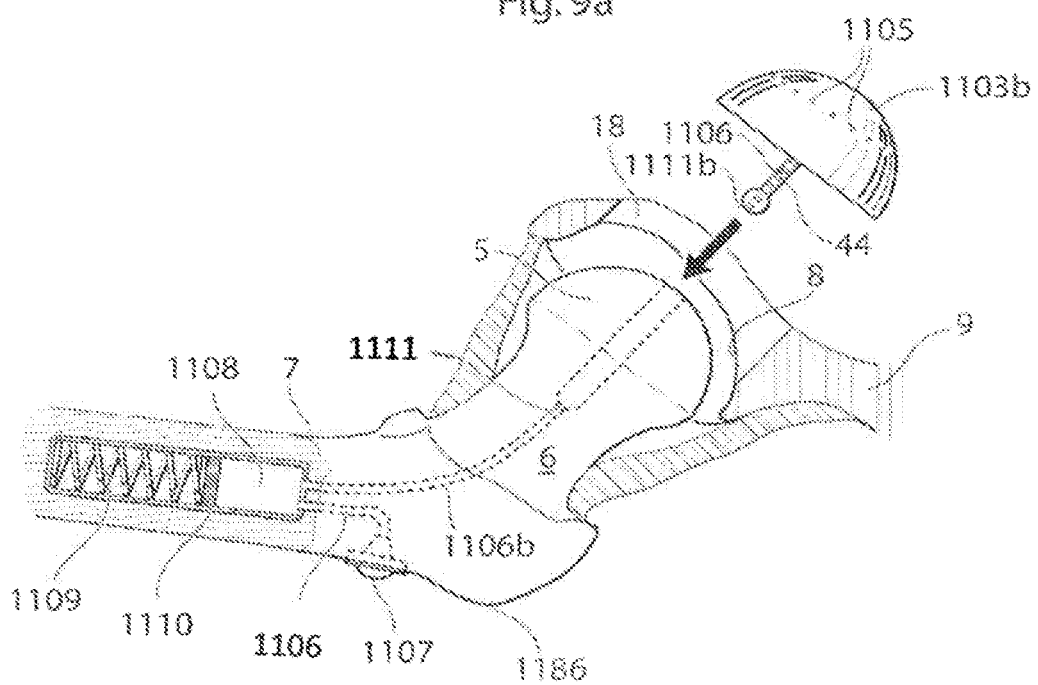
FIG. 9a shows the hip joint in section when a medical device is being provided through a hole in the pelvic bone.

FIG. 9a shows a hip joint in section when a medical device is being provided, through a hole 18 in the pelvic bone 9 for replacing the contacting surface of the caput femur 5. The medical device comprises an artificial contacting surface 1103b and a fixating portion 44 placed centrally in the medical device and adapted to fixate the medical device to the caput femur 5. The medical device comprises a plurality of channels 1105 which exits at the artificial contacting surface for lubricating the hip joint. The channels are in fluid connection with a conduit 1106 which in turn is connected to an interconnecting part 1111b adapted to connect the conduit to a second conduit 1106b or a second portion of the conduit 1106b, which in turn is in fluid connection with a reservoir 1108 placed in the femoral bone 7 of the human patient. The reservoir 1108 is placed in the femoral bone 7 and is adapted to hold a pressurized lubricating fluid, which according to the embodiment shown in FIG. 9a is pressurized by means of said reservoir 1108 being spring loaded by means of a spring 1109 in connection with a movable wall portion in the form of a piston 1110 pressurizing the lubricating fluid. The reservoir 1108 is furthermore connected to an injection port 1107 which is positioned in connection with the femoral bone 7 below the greater trochanter 1186, however, any other suitable placement is also conceivable, in connection with bone, in a cavity or subcutaneously. The medical device is according to the embodiment of FIG. 9*a* operable using a pressurized reservoir, however according to other embodiments the medical device is operable by a powered operating device, such as an implantable pump, which could be powered by direct propulsion, such as inductive or magnetic propulsion, or by an accumulated energy source, such as a battery. The channels or conduits could according to one embodiment (not shown) comprise a valve for closing the flow of lubricating fluid through the conduit 1106 or channel 1105, thereby closing the connection between the reservoir and the artificial contacting surface. The valve could be powered and adapted to be controlled form outside of the human body by means of for example a remote control.

Figure 9B:
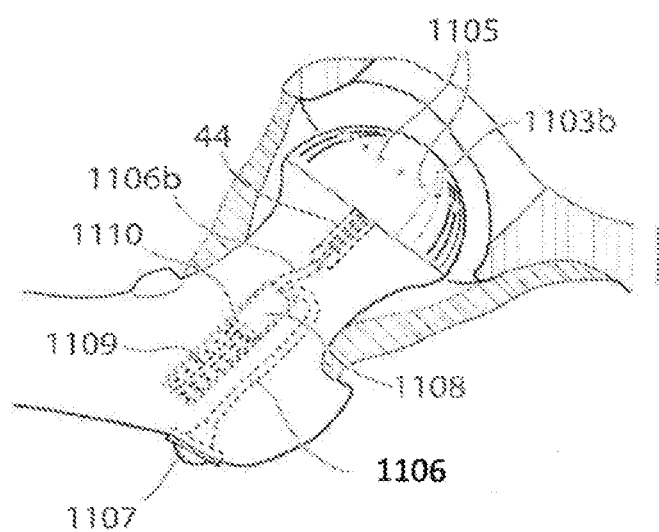
FIG. 9b shows the hip joint in section when a medical device has been provided through a hole in the pelvic bone.

FIG. 9*b* shows the hip joint in section when a medical device according to another embodiment has been provided to the hip joint, replacing the contacting surface of the caput femur. The medical device comprises an artificial contacting surface 1103*b* comprising a plurality of channels 1105 which are connected to a conduit 1106, 1106*b* placed in fixating part of the medical device. The conduit is in turn in fluid connection with a reservoir 1108 placed inside of the femoral bone, preferably in the cancellous parts of the femoral bone, the reservoir is thereby in fluid connection with the channels of the medical device for lubricating the artificial contacting surface 1103*b* of the medical device.

Figure 10:
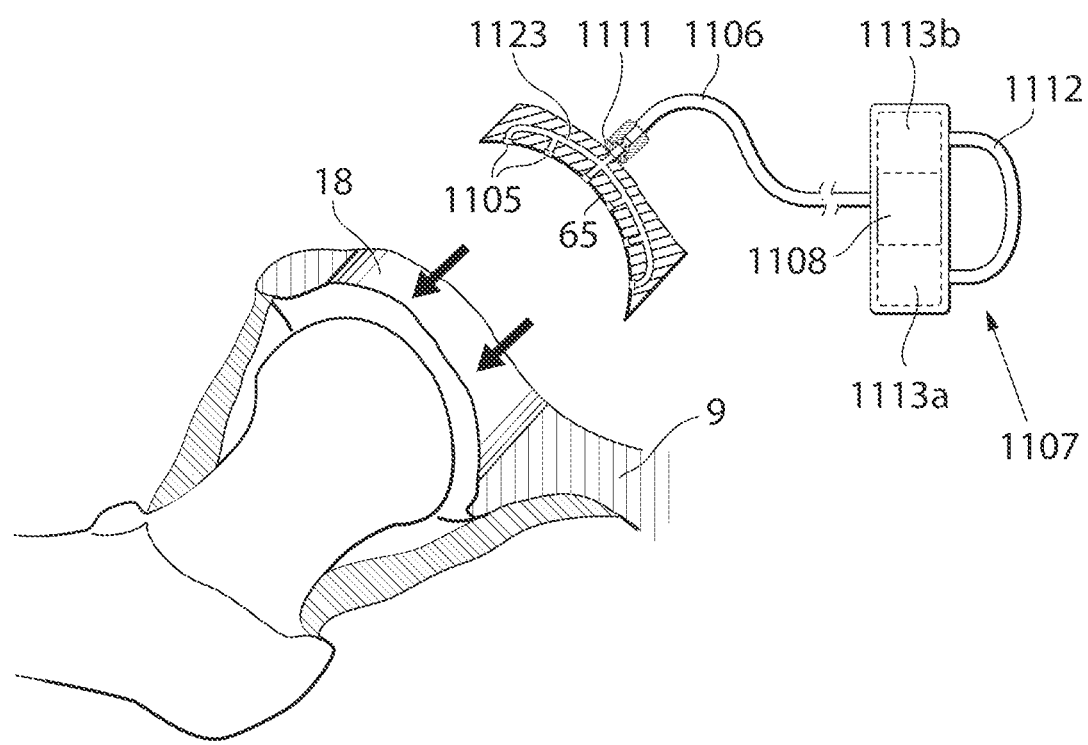
FIG. 10 shows the hip joint is section when a medical device connected to an implantable lubrication system is being provided.

FIG. 10 shows the hip joint in section when an implantable medical device adapted to replace the acetabulum contacting surface is being provided. The medical device comprises an artificial acetabulum surface 65 comprising a plurality of channels connected to a conduit 1106 by an inter-connecting part 1111. The medical device is according to the embodiment shown in FIG. 10 adapted to be placed in a hole 18 in the pelvic bone 9 for replacing the acetabulum contacting surface 65. FIG. 10 furthermore shows a unit to which the conduit 1106 is connected, according to one embodiment the unit comprises a reservoir 1108 and two pressure creating devices 1113*a*, 1113*b* adapted to create a pressure for pressurizing the lubricating fluid for pressing said lubricating fluid through the conduit 1106 and further through the plurality of channels 1105 for lubricating the implantable medical device. The conduit 1106 transports lubricating fluid to the inlet 1123 for further distribution to the channels 1105. The pressure creating devices could be spring loaded or comprise of a pressurized gas filled element which is further pressurized by the injecting of a lubricating fluid into the reservoir 1108. The unit further comprises an injection port 1107 which comprises a self sealing membrane 1112, which preferably is a Parylene coated silicone membrane. According to another embodiment the unit comprises a powered operation device such as a pump housed in the container 1113*a* which pumps the lubricating fluid from the reservoir 1108 through the conduit 1106 to the plurality of channels 1105. According to one embodiment the pump is powered by a battery housed in the compartment 1113*b*.

FIG. 11*a* shows a surgical instrument adapted to insert a medical device according to any of the embodiments herein, or a mould for creating a medical device, according to a first embodiment. The surgical instrument comprises a gripping portion 76 and a handling portion 77. According to the embodiments shown in FIG. 11*a,b,c* the instrument further comprises a rotation element 78 that enables the gripping part 76 to rotate in relation to the handling part 77, however it is equally conceivable that the surgical instrument lacks this rotation element 78.

FIG. 11*b* shows the surgical instrument adapted to insert a prosthesis, prosthetic parts or parts needed to create or provide a hip joint surface, according to a second embodiment. According to this embodiment the surgical instrument further comprises a parallel displaced section 79, which increases the reach of the instrument and facilitates the reaching of the hip joint through a hole in the pelvic bone from the opposite side from acetabulum.

FIG. 11*c* shows the surgical instrument adapted to insert a prosthesis, prosthetic parts or parts needed to create or provide a hip joint surface, according to a third embodiment. According to this embodiment the surgical instrument further comprises two angle adjusting members 80*a,b*. The angle adjusting members could be adjustable for varying the angle of said gripping part 76 in relation to the handling portion 77, or fixed in an angle suitable for creating operating in a hip joint through a hole in the pelvic bone from the opposite side from acetabulum 8.

FIG. 12 shows the hip joint in section when a medical device has been provided. The implantable medical device is adapted to replace the acetabulum surface and is inserted through a hole 18 in the pelvic bone 9, however, in other embodiments it is equally conceivable that the medical device is adapted to be inserted through a hole in the femoral 7 bone or the hip joint capsule. The medical device comprises a plurality of channels 1105 interconnected through a conduit 1106 which places the channels 1105 in fluid connection with each other. The conduit 1106 transports lubricating fluid to the inlet 1123 for further distribution to the channels 1105. The conduit 1106 is further connected to a first portion of an interconnecting part 1111 which is adapted to be connected to a second portion of an interconnecting part 1111*b*. The interconnecting part 1111 connects a first portion of the conduit 1106 to a second portion of the conduit 1106, enabling a first portion of the conduit 1106 to be inserted from the acetabulum side of the pelvic bone 9 and a second portion of the conduit 1106 to be inserted from the pelvic side, or opposite acetabulum side of the pelvic bone 9. The connection of two portions of the conduit 1106 is particularly beneficial when the medical device has been inserted through a hole 18 in the femoral bone 7 or the hip joint capsule and the reservoir 1108 is implanted in the abdominal region of the human patient, or in another area on the abdominal side of the pelvic bone 9. The conduit 1106 is then further connected to the reservoir 1108 and adapted to transport a lubricating fluid from the reservoir 1108 to an area of the hip joint. The reservoir 1108 is according to the embodiment shown in FIG. 12 adapted to place the lubricating fluid under pressure by means of a spring 1109 exerting a force on a movable wall portion in the form of a piston 1110 pressing the lubricating fluid through the conduit 1106 and further through the channels 1105. The reservoir 1108 further comprises an injection port 1107 placed in the top part of the reservoir 1108 for refilling the reservoir 1108 and in the same event increasing the pressure of the lubricating fluid.

Figure 13A:
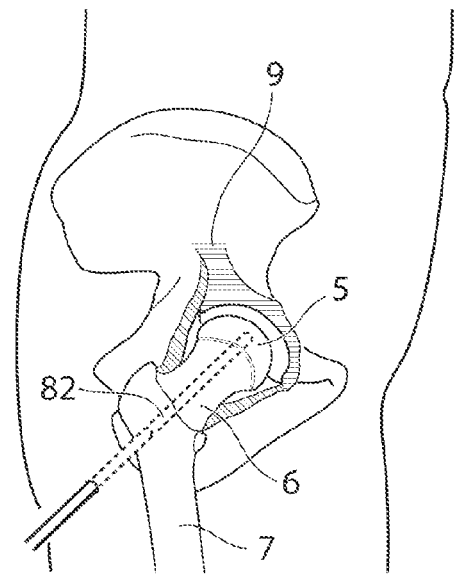
FIG. 13a shows the lateral view of a hip joint ion section when a hole is being created through the femoral bone.

FIG. 13*a* shows a human patient in a lateral view showing the hip joint in section. The femoral bone 7 has a proximal part comprising the collum femur 6 and most proximal the caput femur 5. In FIG. 13*a* a hole 82 is being created from an incision made in the thigh, the hole travels into the femoral bone 7, following the collum femur 6 and exiting through the caput femur 5 and thus into the hip joint. The hole is used to provide the hip joint with a medical device which preferably is possible to roll or bend for insertion through said hole 82.

Figure 13B:
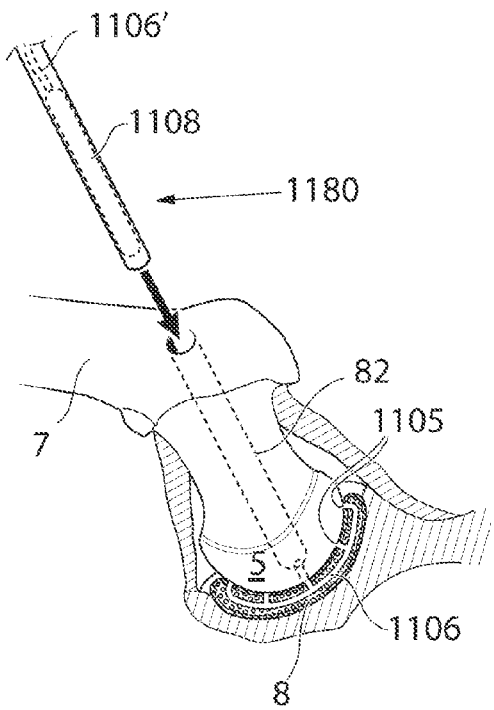
FIG. 13b shows a hip joint in section when a medical device is being provided through a hole in the femoral bone.

FIG. 13b shows the hip joint in section when the medical device has been provided through the hole 82 in the femoral bone 7 and fixated in the acetabulum bowl 8. The medical device comprises a plurality of channels 1105 connected to each other by a conduit 1106. According to other embodiments, the medical device could be provided through the hip joint capsule, or a hole in the pelvic bone 9. After the medical device has been provided, a tool 1180 housing a reservoir 1108 connected to a conduit 1106' is used to provide the reservoir 1108 to the hole 82 in the femoral bone 7 and to connect the reservoir to the conduit 1106 of the medical device.

Figure 13C:
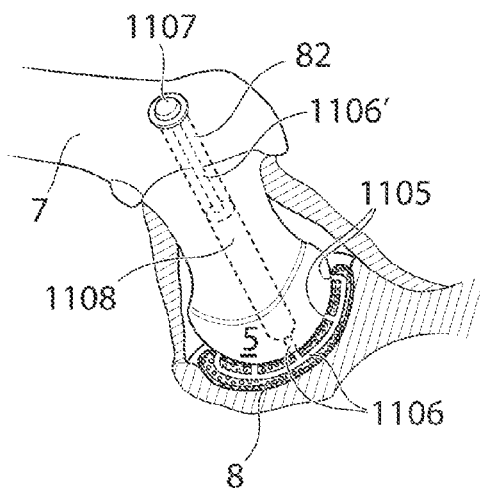
FIG. 13c shows a hip joint in section when a medical device has been provided through a hole in the femoral bone.

FIG. 13c shows the hip joint in section when the reservoir 1108, placed in the hole 82 in the femoral bone 7 has been connected to the medical device. Furthermore a conduit 1106' reaching from the reservoir 1108 to an injection port 1107 for refilling and/or pressurizing the reservoir 1108.

Figure 13D:
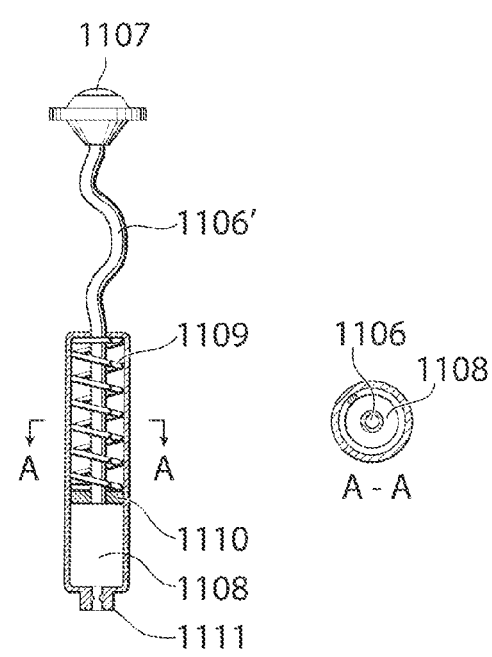
FIG. 13d shows a reservoir adapted to be connected to a medical device, in further detail.

FIG. 13d shows the reservoir unit in further detail, the reservoir unit comprises an inter-connecting portion 1111 placed at the end part of the reservoir unit, a pressurized reservoir 1108, which according to the embodiment of FIG. 13d is pressurized by means of a spring 1109 pushing a movable wall portion 1110 in the form of a piston 1110. The reservoir unit further comprises a conduit 1106' in connection with the reservoir, and in connection with an injection port 1107, for filling the and/or pressurizing the reservoir 1108 comprising the lubricating fluid. The injection port 1107 comprises a self sealing membrane, which could be a self sealing Parylene coated silicone membrane, to inhibit cell migration on the surface of the injection port. The section A-A shows the centrally placed conduit 1106 in the center of the reservoir 1108 for filling and/or pressurizing the reservoir 1108.

Figure 14:
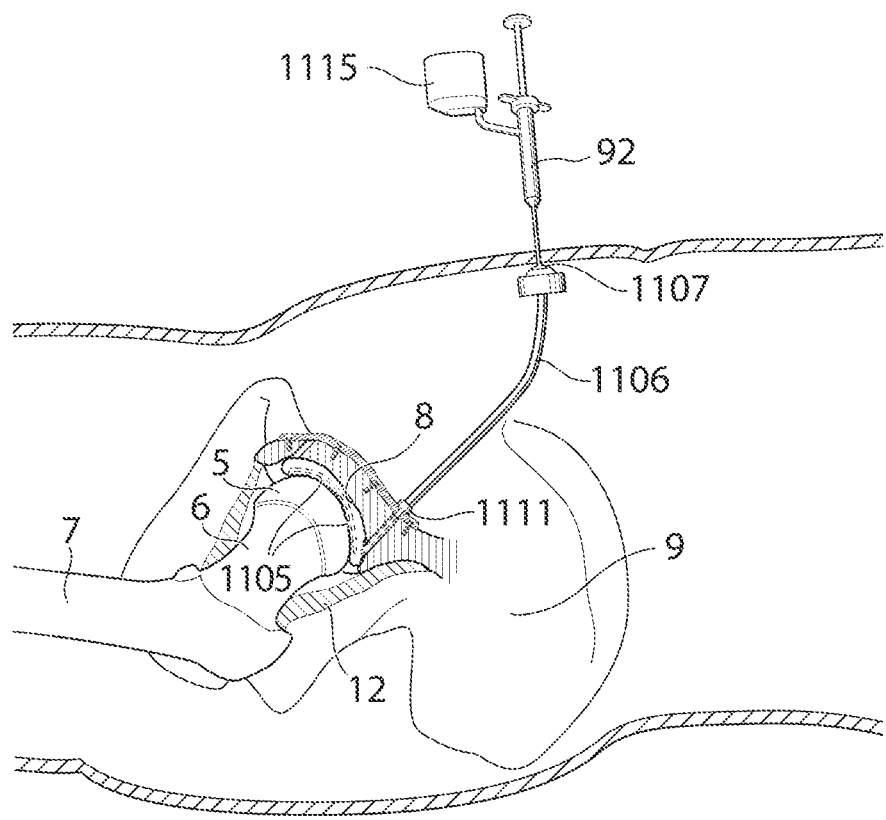
FIG. 14 shows the injection of a lubricating fluid into an implantable injection port.

FIG. 14 shows a lateral view of a human patient in section, when a lubricating fluid is being injected into an injection port 1107, by means of an injecting member 92 comprising a container 1115 adapted to contain the lubricating fluid to be injected. The injection port is connected to an implantable medical device placed in the hip joint through a conduit 1106 adapted to supply the fluid connection between the injection port and the medical device. The medical device in turn comprises a plurality of channels 1105 for lubricating the artificial contacting surfaces and thereby lubricating the hip joint. According to the embodiment shown in FIG. 14 the medical device has been supplied from the abdominal side of the pelvic bone 9 through a hole made in the pelvic bone which afterwards has been refilled with the removed bone plug and sealed and fixated with a mechanical fixating part attached with screws. According to other embodiments the medical device is provided from the hip joint side of the pelvic bone 9 through the hip joint capsule 12 or the femoral bone 7 and thereafter connected to the conduit 1106 on the abdominal side of the pelvic bone 9 through an interconnecting part 1111. This enables the placing of the injection port 1107 in the abdominal region, subcutaneously, in a cavity and/or supported by the muscular or fascia tissue.

Figure 15:
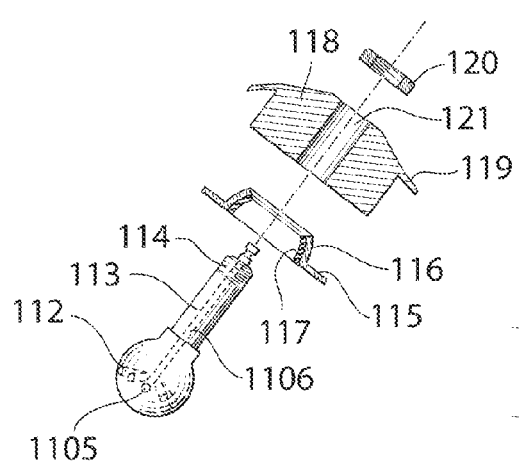
FIG. 15 shows an implantable medical device in an opposite embodiment.

FIG. 15 shows the medical device in an opposite embodiment where the medical device comprises a first artificial contacting surface 112 comprising a convex shape towards a centre of the hip joint. The first artificial contacting surface 112 is adapted to be fixated to the pelvic bone 9 of the human patient. The artificial convex hip joint surface 112 is adapted to be fixated to the pelvic bone 9, and is adapted to be inserted through a hole 18 in the pelvic bone 9. The medical device comprises a nut 120, comprising threads for securely fixating the medical device to the pelvic bone 9. The medical device further comprises a prosthetic part 118 adapted to occupy the hole 18 created in the pelvic bone 9 after the medical device has been implanted in the patient. The prosthetic part 118 comprises supporting members 119 adapted to be in contact with the pelvic bone 9 and assist in the carrying of the load placed on the medical device from the weight of the human patient in normal use. Normal use is defined as the same as a person would use a natural hip joint. Further the medical device comprises a locking element 116 comprising a surface 117 adapted to be in contact with the artificial convex hip joint surface 112. The locking element 116 further comprises fixating members 115 which are adapted to assist in the fixation of the locking member 116 to the caput femur 5 or collum femur 6, which in turns fixates the artificial convex hip joint surface 112. The artificial convex hip joint surface 112 is fixated to a attachment rod 113 comprising a thread 114 that corresponds to the thread of the nut 120 in connection with the prosthetic part 118. The medical device comprises a plurality of channels 1105 adapted to lubricate the artificial contacting surface 112. The plurality of channels 1105 are connected to each other through a conduit 1106 adapted to transport a lubricating fluid from a reservoir 1108 to the plurality of channels 1105 which are fully integrated in the artificial contacting surface 112 of the medical device for lubricating the artificial contacting surface 112 and thereby lubricating the hip joint.

Figure 16:
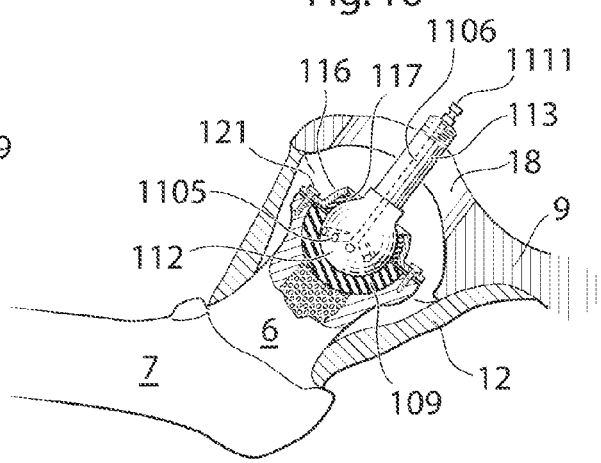
FIG. 16 shows a hip joint in section, when an implantable medical device in an opposite embodiment has been placed.

FIG. 16 shows the medical device according to FIG. 15 when said medical device is placed inside of the hip joint. The first artificial contacting surface 112 comprising a convex shape towards a centre of the hip joint is positioned in a second artificial contacting surface 109 comprising a concave shape towards the centre of the hip joint. The second artificial contacting surface 109 is placed and fixated in the caput 5 and collum femur 6 of the femoral bone an secured by a locking element 116 comprising a surface 117 facing the first artificial convex contacting surface 112. The medical device comprises a plurality of channels 1105 which are connected to a conduit 1106 placed centrally in the medical device for providing a lubricating fluid to the medical device and lubricate the artificial contacting surface 112 and thereby the hip joint.

Figure 17:
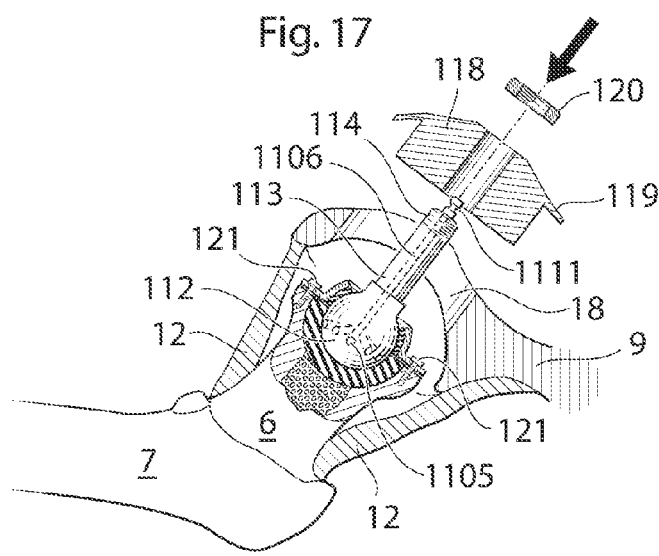
FIG. 17 shows a hip joint in section, when an implantable medical device in an opposite embodiment has been placed.

FIG. 17 shows the providing of a prosthetic part 118 to the hole 18 in the pelvic bone 9. The prosthetic part 118 comprises supporting members 119 adapted to be in contact with the pelvic bone 9 and assist in the carrying of the load placed on the medical device from the weight of the human patient in normal use.

Figure 18:
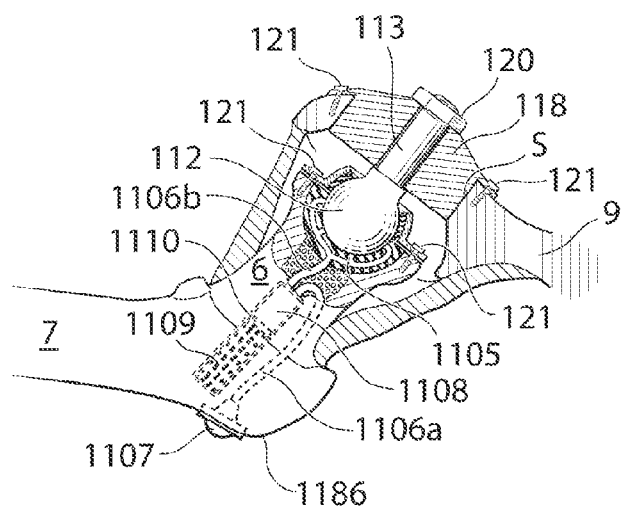
FIG. 18 shows a hip joint in section, when an implantable medical device in an opposite embodiment has been placed and connected to a reservoir.

FIG. 18 shows an alternative embodiment of the medical device in the opposite embodiment in which the part of the medical device comprising an artificial concave hip joint surface placed in the caput 5 and collum femur 6 comprises a plurality of lubricating channels 1105 which are connected to a conduit 1106b establishing a fluid connection between the medical device and the reservoir located in the cancellous bone of the collum femur 6. The reservoir is adapted to be refilled through an injection port 1107 which according to the embodiment of FIG. 18 is placed in connection with the femoral bone 7 and situated below the greater trochanter 1186. The reservoir unit, and the function thereof, is described in further detail with reference to FIGS. 9a and 9b. FIG. 18 furthermore shows the prosthetic part 118, when fixated to the pelvic bone 9 using screws 121. The screws could be assisted or replaced by an adhesive which could be applied in connection to the screws or at the surface S between the prosthetic part and the pelvic bone 9.

Figure 19:
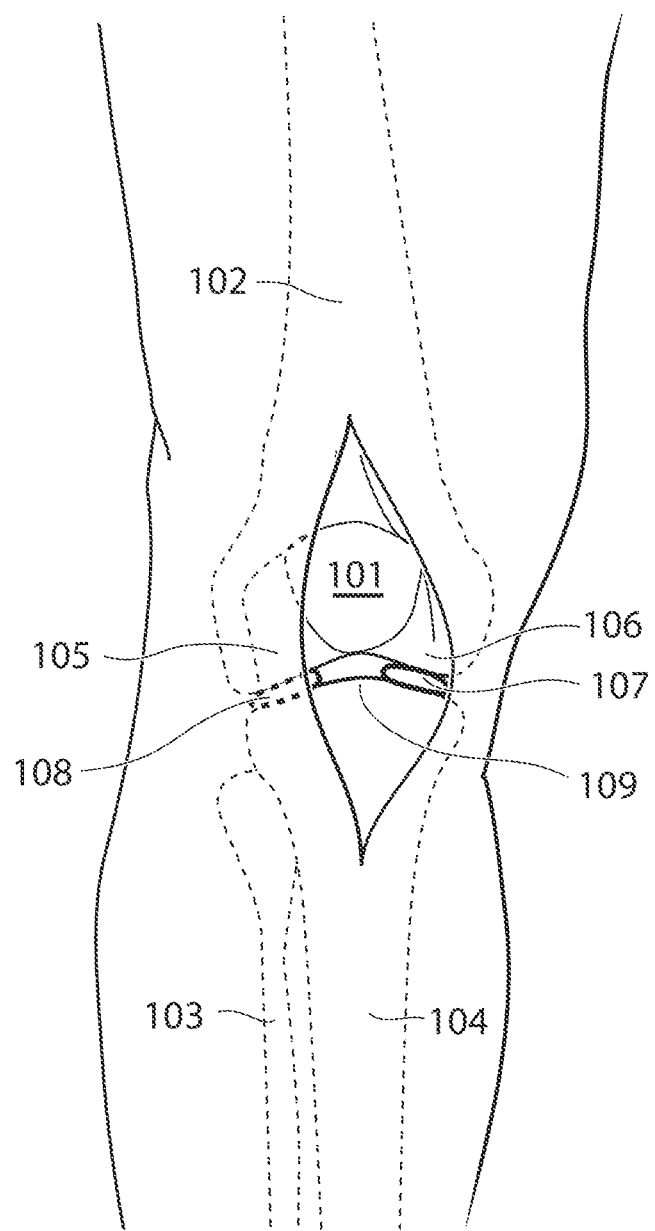
FIG. 19 shows a frontal view of a knee joint of a human patient.

FIG. 19 shows the right leg of a human patient. The femoral bone 102 having a distal part comprising the lateral condyle 105, the medial condyle 106 and an area between said lateral and said medial condyle 131. The sections of the distal part of the femoral bone 102 comprise contacting surfaces of the knee joint. The knee joint furthermore comprises the patella 101, which is a triangular bone which articulates with the femur 102 and covers and protects the knee joint. The knee joint also comprises the minisci 107, 108 which are cartilaginous elements within the knee joint which serve as articulating surfaces to protect the ends of the bones from rubbing on each other. The minisci 107, 108 also acts as shock absorbers in the knee joint, to absorb the shocks from the movement of the human patient. There are two menisci 107,108 in each knee, the medial meniscus 107 and the lateral meniscus 108. In patients with osteoarthritis the menisci 107, 108 which acts as articulating surfaces i.e. weight carrying surfaces are worn away and, in extreme cases, bone can be exposed in the joint. The knee joint is protected by the knee joint capsule also known as the articular capsule of the knee joint or the capsular ligament of the knee joint. The knee joint capsule is wide and lax; thin in front and at the side; and contains the patella 101, ligaments, menisci 107,108, and bursae, which are small fluid-filled sacs made of white fibrous tissue. The knee joint capsule consists of a synovial and a fibrous membrane separated by fatty deposits anteriorly and posteriorly.

Figure 20:
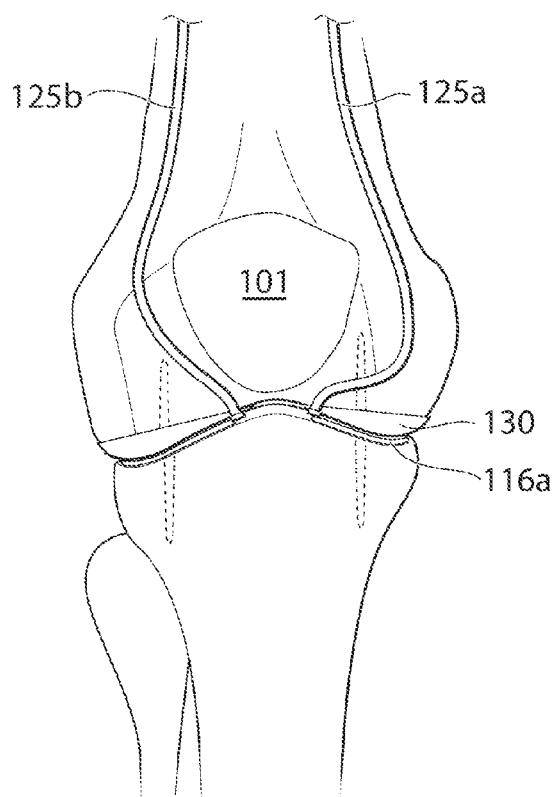
FIG. 20 shows a frontal view of a knee joint of a human patient, when a medical device has been provided.

FIG. 20 shows the knee joint when artificial knee joint surfaces 130, 116a has been provided to the distal part of the femoral bone 102 and the proximal part of the tibia bone 104. A lateral and medial channel 125a,b supplies the contacting surfaces and thereby the knee joint with lubricating fluid for reducing the friction of the knee joint.

Figure 21:
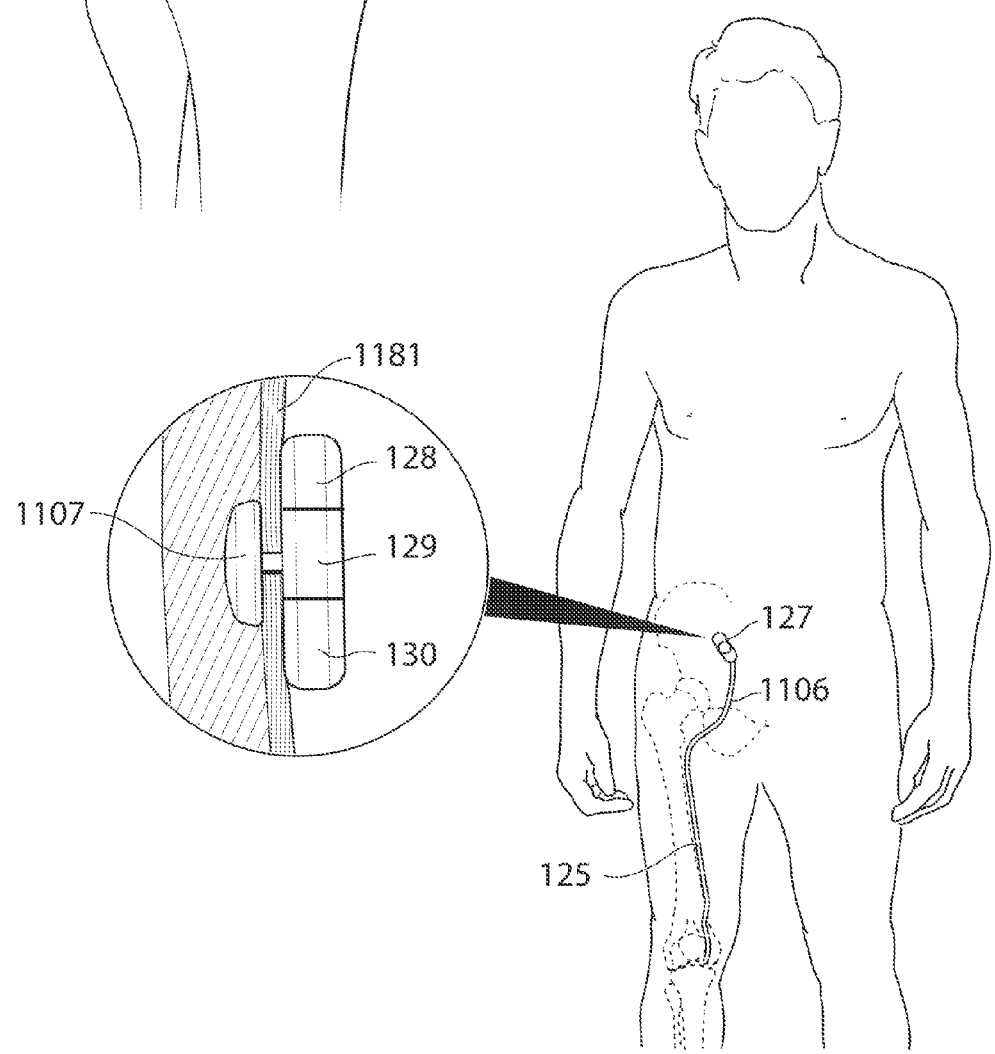
FIG. 21 shows an implantable lubricating system.

FIG. 21 shows the body of a human patient in a frontal view where a reservoir unit 127 is implanted subcutaneously in the abdominal region of the human patient. The reservoir unit according to this embodiment comprises an operating device in the form of a pump 130 which is powered by a battery 128 for pumping a fluid from the reservoir 129 through a conduit to a channel 125 supplying the artificial contacting surfaces of the knee joint with a lubricating fluid. The reservoir unit is fixated to the muscular or fascia tissue 1181 of the abdominal wall through the muscular or fascia 1181 tissue being clamped between the reservoir unit and the injection port 1107 arranged at the outside of the muscular or fascia tissue 1181.

Figure 22A:
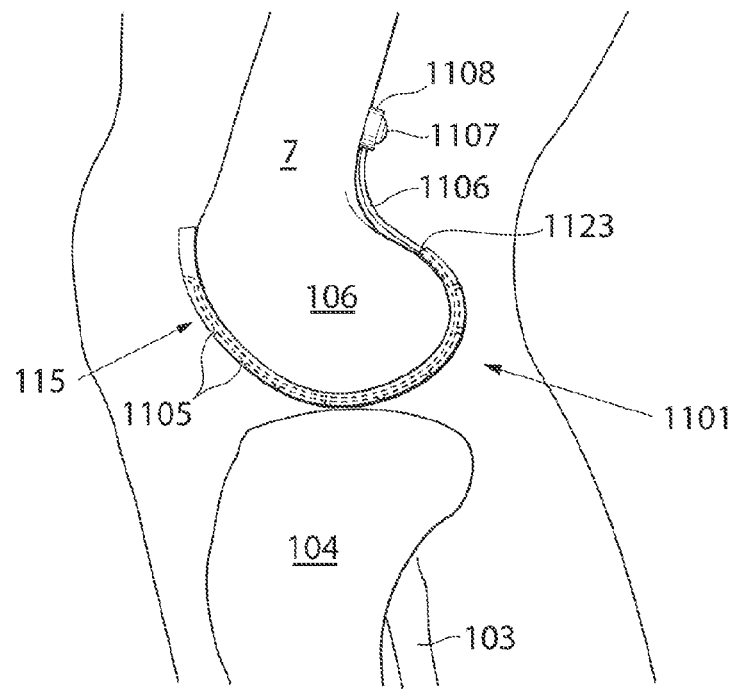
FIG. 22a shows a lateral view of a knee joint when a medical device has been provided to the femoral bone.

FIG. 22a shows an embodiment where the medical device comprises an artificial knee joint 115 surface clamps the medial, lateral or both the medial and lateral condyle 106 of the knee joint, being the distal portion of the femoral bone 7. The medical device, according to this embodiment comprises a plurality of channels 1105 for lubricating the artificial contacting surfaces, the plurality of channels are in fluid connection with each other through a conduit 1106 which in turn is in fluid connection with a reservoir 1108 comprising an injection port 1107 for refilling the reservoir or pressurizing the lubricating fluid contained in said reservoir 1108. The conduit 1106 transports lubricating fluid to the inlet 1123 for further distribution to the channels 1105.

Figure 22B:
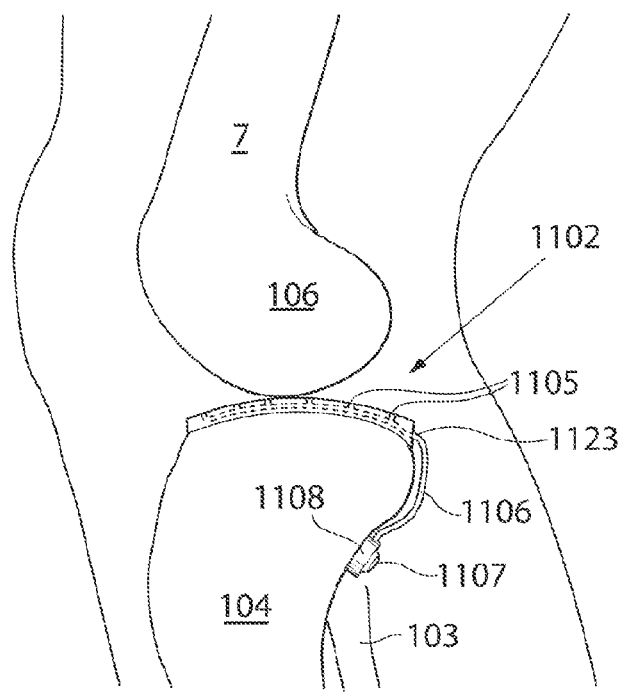
FIG. 22b shows a lateral view of a knee joint when a medical device has been provided to the tibia bone.

FIG. 22b shows the knee joint in a lateral view when a medical device comprising an artificial contacting surface 1102 has been provided to the proximal part of the tibia bone 104, which together with the fibula bone 103 makes up the lower part of the leg. The artificial knee joint surface comprises a plurality of channels 1105 which are in fluid connection with a conduit 1106 adapted to transport lubricating fluid from a reservoir 1108. The reservoir 1108 is according to the embodiment of FIG. 22b placed at the rear side of the tibia bone 104 and fixated to the tibia bone 104 and comprises an injection port 1107 for injecting a lubricating fluid into the reservoir 1108 and/or pressurizing a lubricating fluid contained in the reservoir 1108. The conduit 1106 transports lubricating fluid to the inlet 1123 for further distribution to the channels 1105.

Figure 23:
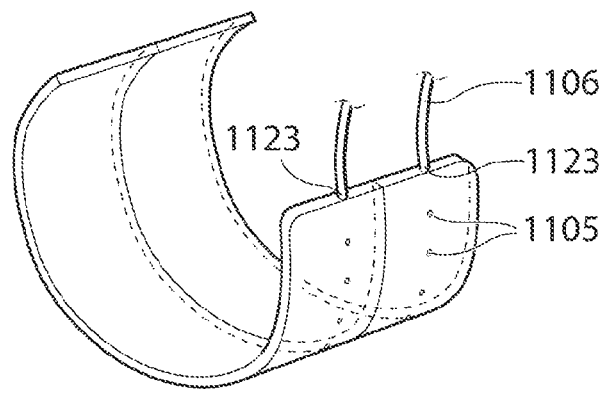
FIG. 23 shows a medical device comprising an artificial knee joint surface.

FIG. 23 shows the medical device for implantation in a knee joint in further detail. The medical device comprises a plurality of channels 1105 placed along the artificial contacting surface of the medical device, for lubricating the contacting surface of the medical device. The channels 1105 are connected to a conduit 1106 for transport of the lubricating fluid along the artificial contacting surface 1101 of the medical device. The conduit 1106 transports lubricating fluid to the inlets 1123 for further distribution to the channels 1105.

Figure 24:
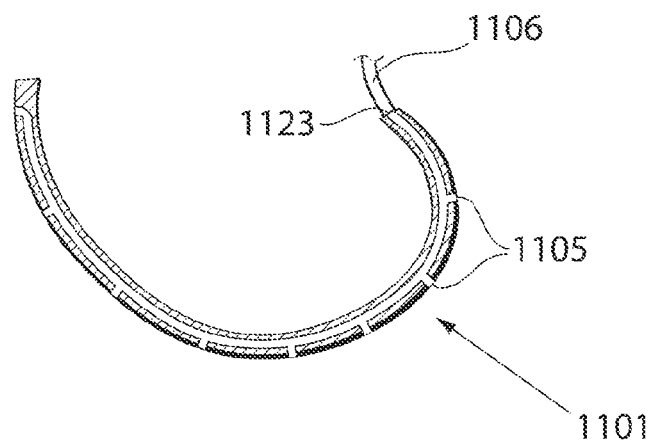
FIG. 24 shows a medical device comprising an artificial knee joint surface in section.

FIG. 24 shows a sectional side-view of the medical device displaying the channels 1105 being fully integrated in the artificial contacting surface and connected to each other, the conduit 1106 supplies the 1105 channels with lubricating fluid for lubricating the artificial contacting surface of the medical device. The conduit 1106 transports lubricating fluid to the inlet 1123 for further distribution to the channels 1105.

Figure 25A:
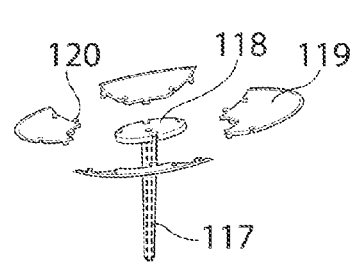
FIG. 25a shows a medical device comprising multiple medical device parts.

FIG. 25a shows a medical device for implantation in a knee joint of a human patient, the medical device comprises a several medical device parts 119 adapted to be connected to each other and to a medical device base part 118 by means of mechanical fixation elements 120 supplying a form fitting between the plurality of medical device parts 119 and the base part 118. The medical device base part 118 furthermore comprises a fixation portion 117 which is adapted to supply mechanical fixation of the medical device to a human bone, such as the proximal part of the tibia bone. The medical device base part 118 furthermore comprises a channel for supplying a lubricating fluid to the artificial contacting surface of the knee joint.

Figure 25B:
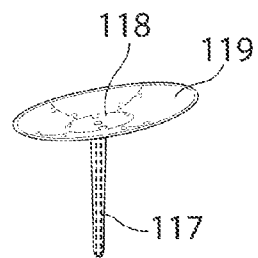
FIG. 25b shows a medical device comprising multiple medical device parts, when assembled.

FIG. 25b shows the medical device according to FIG. 25a, when assembled.

Figure 26:
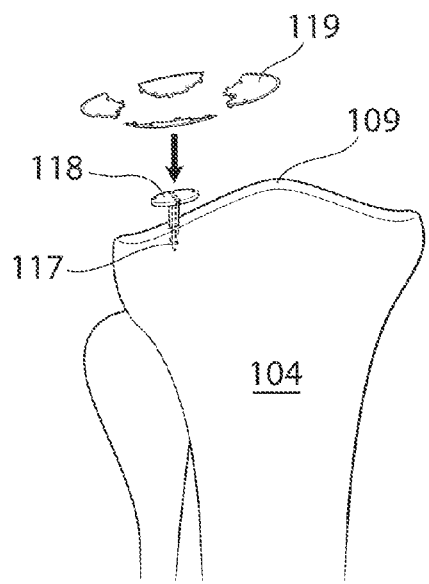
FIG. 26 shows the placing of a medical device comprising multiple medical device parts, when being fixated to the tibia bone.

FIG. 26 shows the medical device according to FIGS. 25a and 25b when the medical device is being fixated to the tibia bone 104.

Figure 27:
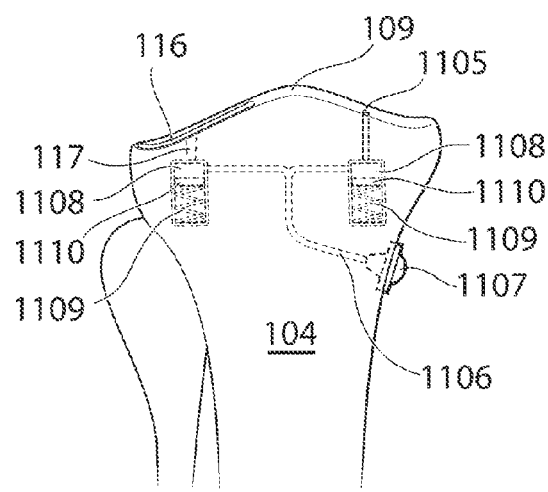
FIG. 27 shows the implantable medical device according to an embodiment, when fixated to the tibia bone and connected to a reservoir and an injection port.

FIG. 27 shows the proximal part of the tibia bone when a medical device comprising an artificial contacting surface 116 has been fixated to the tibia bone 104. The channel 1105 of the artificial contacting surface is connected to a conduit 1106 which supplies a fluid connection between the channel 1105 of the medical device and a first and second reservoir 1108 placed inside of the tibia bone 104 on the medial and lateral side. The conduit further connects the first and second reservoir to an injection port 1107 placed on the medial side of the pelvic bone for refilling and/or pressurizing the reservoirs 1108. The reservoirs 1108, according to the embodiment shown in FIG. 27 are adapted to place the lubricating fluid under pressure, thereby pressing the lubricating fluid out of the channels 1105 onto the artificial contacting surface, for lubricating the knee joint. For this purpose, the reservoir 1108 comprises a spring 1109 which is in connection with a movable wall portion in the form of a piston 1110, for pressing the lubricating fluid.

Figure 28:
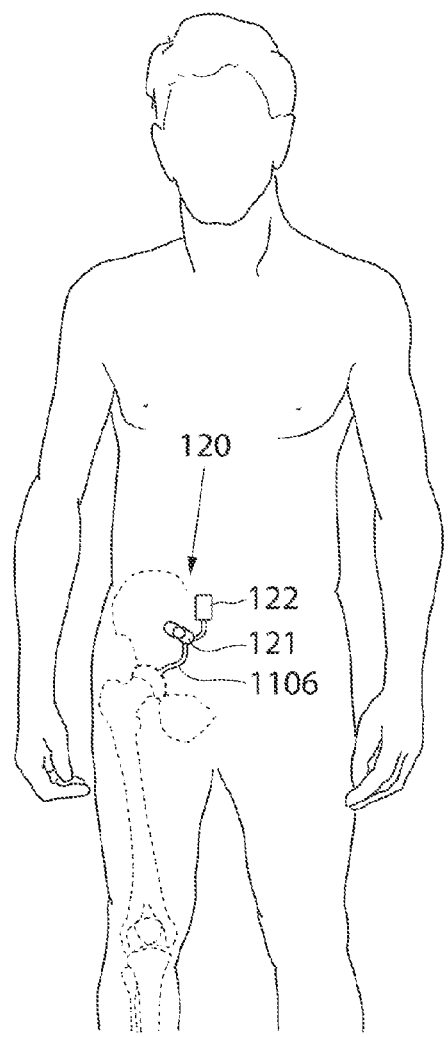
FIG. 28 shows a frontal view of a human patient when an implantable lubricating system has been provided.

FIG. 28 shows the human patient in a frontal view when an implantable lubrication system 120 has been implanted. The implantable lubrication system 120 is adapted to inject a lubricating fluid continuously, intermittently or when needed into said hip joint. According to the embodiment shown in FIG. 61 the implantable lubricating system comprises two interconnected units 121, 122. The two interconnected units are placed in the abdominal region of the human patient and is in connection with the hip joint through a conduit 1106.

Figure 29:
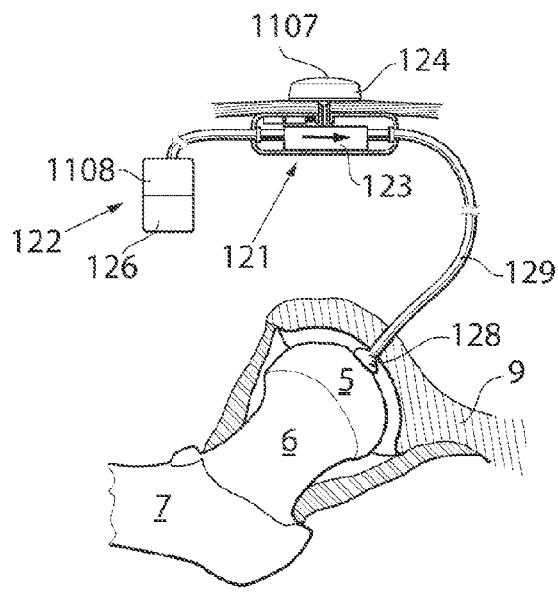
FIG. 29 shows an implantable lubrication system in further detail.

FIG. 29 shows the implantable lubricating system 120, which could be used in combination with any of the medical devices described herein, in further detail. According to the embodiment shown, the implantable lubricating system comprises a first unit 121 comprising a pumping member 123 adapted to pump the lubricating fluid from a reservoir 1108 to an area of the hip joint. The first unit 121 furthermore comprises an injection port 1107 for filling the reservoir 1108 from outside of the human body without having to perform a surgical procedure. The injection port 1107 comprises a self-sealing membrane which is penetratable with a needle attached to a syringe. The first unit 121 further comprises a receiver of wireless energy 124 preferably comprising a coil. Said receiver of wireless energy is used to charge a battery 126. According to this embodiment the implantable lubrication system 120 further comprises a second unit 122 which in turn comprises a battery 126 and a fluid reservoir 1108. The lubricating fluid 128 is pumped from the reservoir 1108, through the first unit 121 with the pumping device, through the conduit 1106 and into the area of the hip joint where it helps lubricating the hip joint surfaces or the artificial contacting surfaces of the implantable medical device. The lubricating fluid is preferably a biocompatible lubricating fluid such as hyaluronic acid.

Figure 30:
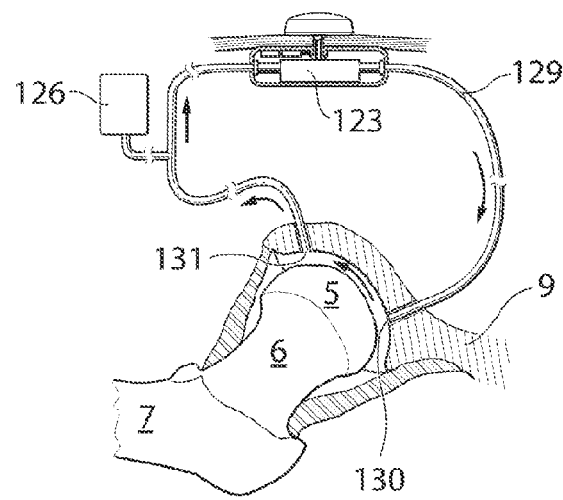
FIG. 30 shows an implantable circling lubrication system in further detail.

FIG. 30 shows the implantable lubricating system adapted to be used with any of the medical device herein, according to an embodiment wherein the implantable lubricating system is a circulating lubricating system comprising one inlet 130 into the joint to be lubricated and one outlet 131. Preferably this system is a system for continuous lubrication where the pumping member 123 continuously circulates the lubricating fluid 128 inside of the hip joint.

Figure 31:
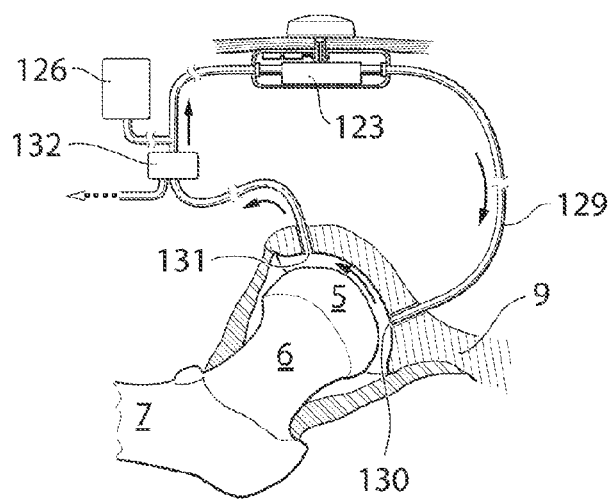
FIG. 31 shows an implantable circling lubrication system comprising a filter, in further detail.

FIG. 31 shows an implantable lubricating system for circulating lubrication adapted to be used with any of the medical device herein, wherein the lubricating system further comprises a filtering member 132 for filtering the lubricating fluid. The filter is adapted to be self cleaning and the out filtered matter is disposed through the disposal channel 133, either into the abdomen of the human patient, or into a container attached to the disposal channel 133. Through the filtering of the lubricating fluid 128 the circulating lubricating system can operate for long periods without the need of any surgical procedures.

Figure 32:
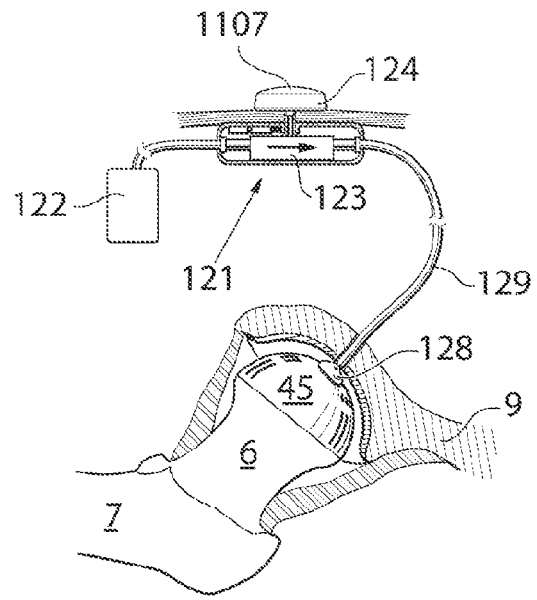
FIG. 32 shows an implantable lubrication system, when lubricating an artificial hip joint surface.

FIG. 32 shows the lubricating fluid of FIG. 29, when lubricating an implantable medical device comprising an artificial contacting surface 45 by providing a lubricating fluid 128.

Figure 33A:
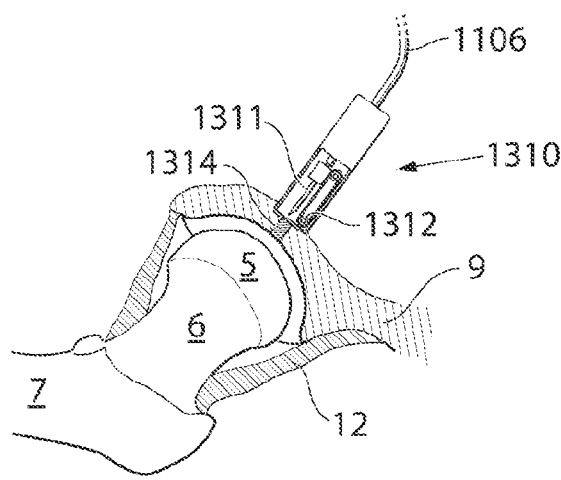
FIG. 33a shows an implantable lubrication system comprising a retractable needle, in a first state.

FIG. 33a shows a lubricating system, which could be adapted to be used in combination with any of the medical devices herein, according to another embodiment wherein the lubricating system comprises a unit 1310 comprising a retractable needle 1311 fixated to an operating system for operating said retractable needle 1311. The needle is adapted to penetrate a self sealing membrane 1314 placed in the pelvic bone 9 for injecting a lubricating fluid into the hip joint. A conduit 1106 is adapted to supply the unit 1310 with a lubricating fluid from an injection port and/or from an additional reservoir which could be implanted subcutaneously or in a cavity of the body.

Figure 33B:
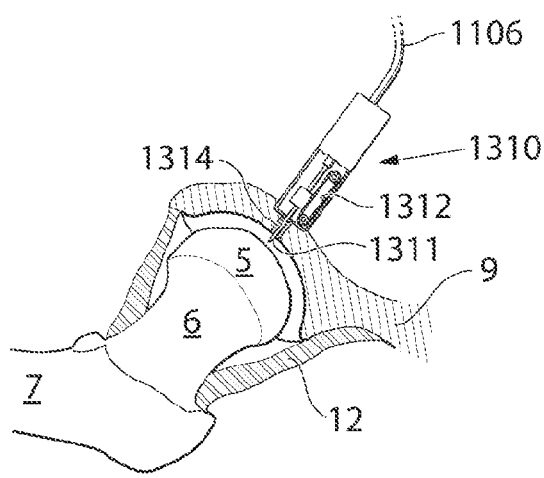
FIG. 33b shows an implantable lubrication system comprising a retractable needle, in a second state.

FIG. 33b shows the lubricating system in a state in which the retractable needle 1311 is in its advanced position by the operating device having operated the retractable needle 1311. The needle thereby penetrates the self sealing membrane 1314 and is placed in a position in which injection of a lubricating fluid is possible.

FIG. 34 illustrates a system for treating a disease comprising an apparatus 10 of the present invention placed in the abdomen of a patient. An implanted energy-transforming device 1002 is adapted to supply energy consuming components of the apparatus with energy via a power supply line 1003. An external energy-transmission device 1004 for non-invasively energizing the apparatus 10 transmits energy by at least one wireless energy signal. The implanted energy-transforming device 1002 transforms energy from the wireless energy signal into electric energy which is supplied via the power supply line 1003.

The implanted energy-transforming device 1002 may also comprise other components, such as: a coil for reception and/or transmission of signals and energy, an antenna for reception and/or transmission of signals, a microcontroller, a charge control unit, optionally comprising an energy storage, such as a capacitor, one or more sensors, such as temperature sensor, pressure sensor, position sensor, motion sensor etc., a transceiver, a motor, optionally including a motor controller, a pump, and other parts for controlling the operation of a medical implant.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 35 illustrates the system of FIG. 34 in the form of a more generalized block diagram showing the apparatus 10, the energy-transforming device 1002 powering the apparatus 10 via power supply line 1003, and the external energy-transmission device 1004, The patient's skin 1005, generally shown by a vertical line, separates the interior of the patient to the right of the line from the exterior to the left of the line.

FIG. 36 shows an embodiment of the invention identical to that of FIG. 35, except that a reversing device in the form of an electric switch 1006 operable for example by polarized energy also is implanted in the patient for reversing the apparatus 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the apparatus 10.

FIG. 37 shows an embodiment of the invention identical to that of FIG. 35, except that an operation device 1007 implanted in the patient for operating the apparatus 10 is provided between the implanted energy-transforming device 1002 and the apparatus 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 38 shows an embodiment of the invention identical to that of FIG. 35, except that it also comprises an operation device in the form of an assembly 1008 including a motor/pump unit 1009 and a fluid reservoir 1010 is implanted in the patient. In this case the apparatus 10 is hydraulically operated, i.e. hydraulic fluid is pumped by the motor/pump unit 1009 from the fluid reservoir 1010 through a conduit 1011 to the apparatus 10 to operate the apparatus, and hydraulic fluid is pumped by the motor/pump unit 1009 back from the apparatus 10 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 39:
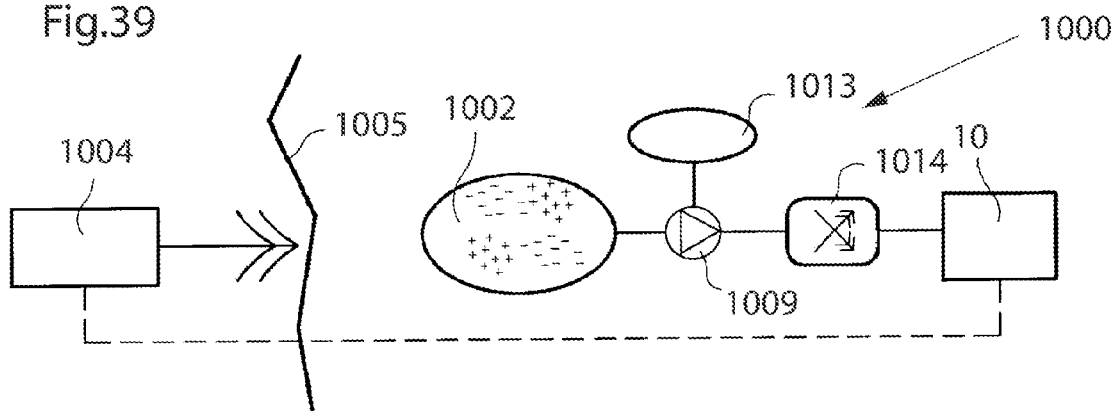

FIG. 39 shows an embodiment of the invention comprising the external energy-transmission device 1004 with its wireless remote control, the apparatus 10, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefor be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the apparatus 10 to operate the apparatus, and another opposite direction in which the fluid is pumped by the motor/pump unit 1009 back from the apparatus 10 to the hydraulic fluid reservoir 1013 to return the apparatus to a starting position.

Figure 40:
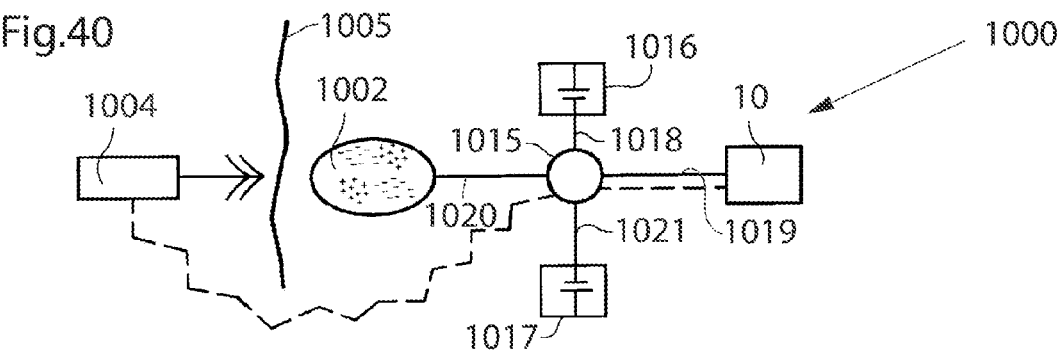

FIG. 40 shows an embodiment of the invention comprising the external energy-transmission device 1004 with its wireless remote control, the apparatus 10, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 1017 in the embodiment of FIG. 40, 10 may be omitted. In accordance with another alternative, the accumulator 1016 in this embodiment may be omitted.

Figure 41:
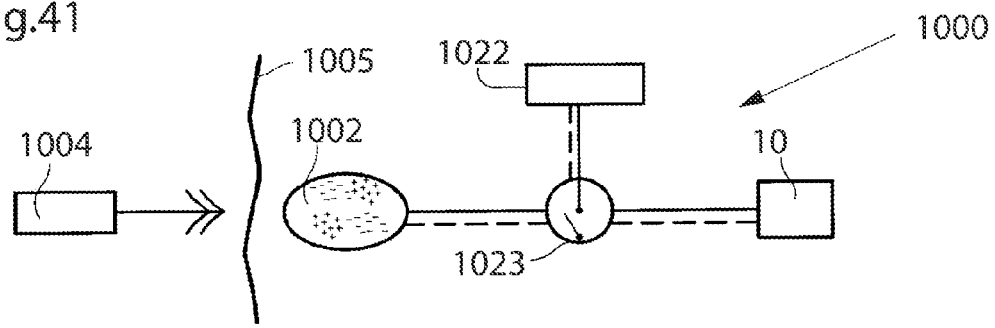

FIG. 41 shows an embodiment of the invention identical to that of FIG. 35, except that a battery 1022 for supplying energy for the operation of the apparatus 10 and an electric switch 1023 for switching the operation of the apparatus 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 10.

Figure 42:
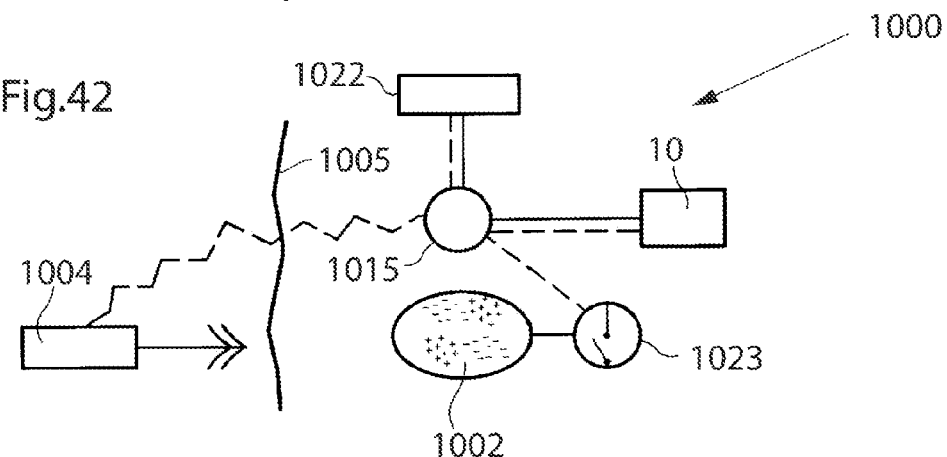

FIG. 42 shows an embodiment of the invention identical to that of FIG. 41, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 10.

Figure 43:
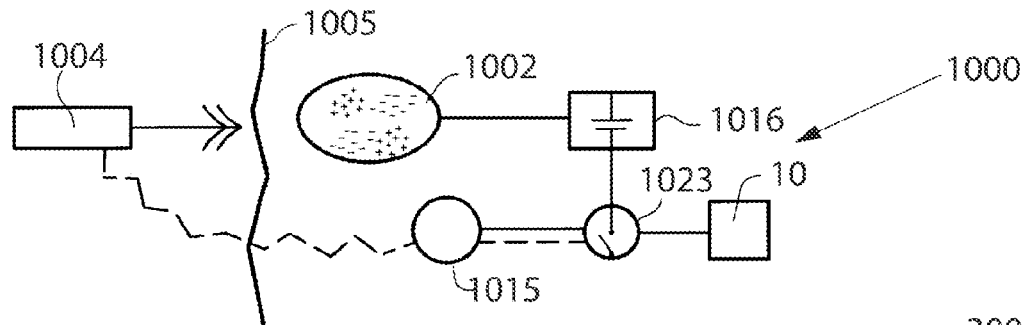

FIG. 43 shows an embodiment of the invention identical to that of FIG. 42, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 44:
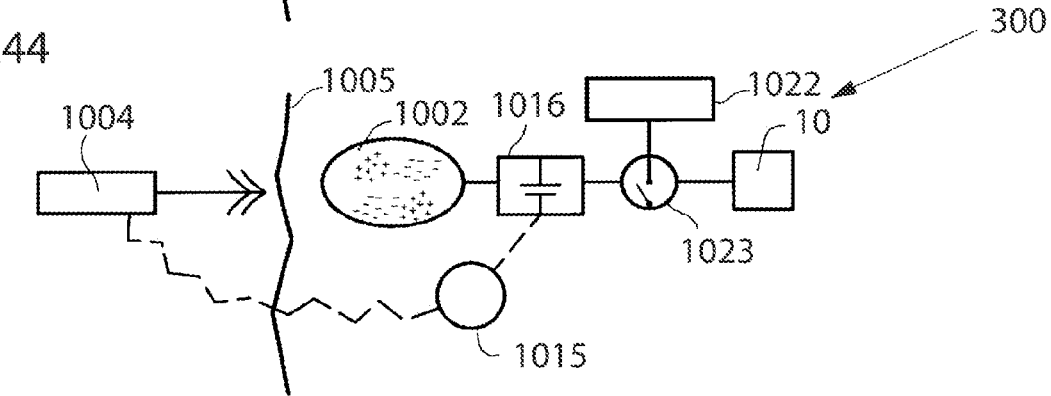

FIG. 44 shows an embodiment of the invention identical to that of FIG. 43, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 10.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 45:
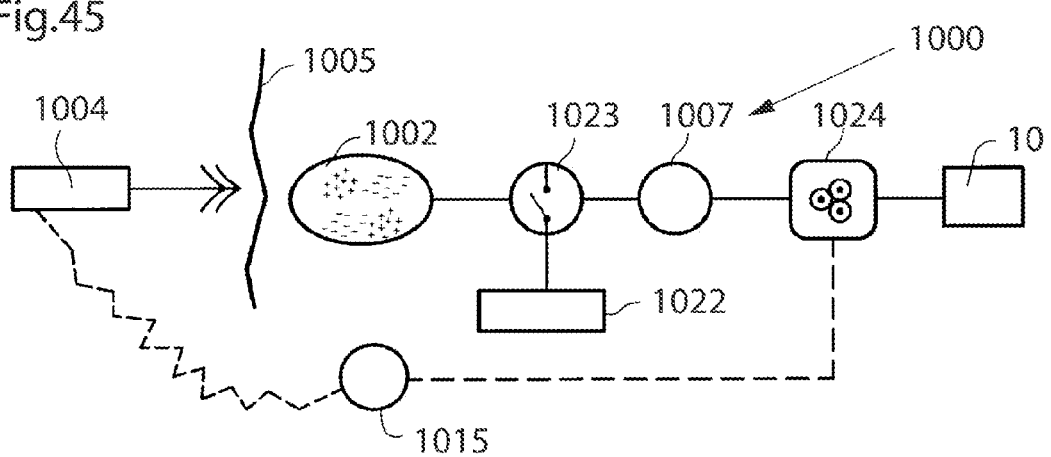

FIG. 45 shows an embodiment of the invention identical to that of FIG. 41, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the apparatus 10 (mechanically operated). Even simpler is to switch the direction of the motor electronically. The gear box interpreted in its broadest embodiment may stand for a servo arrangement saving force for the operation device in favor of longer stroke to act.

Figure 46:
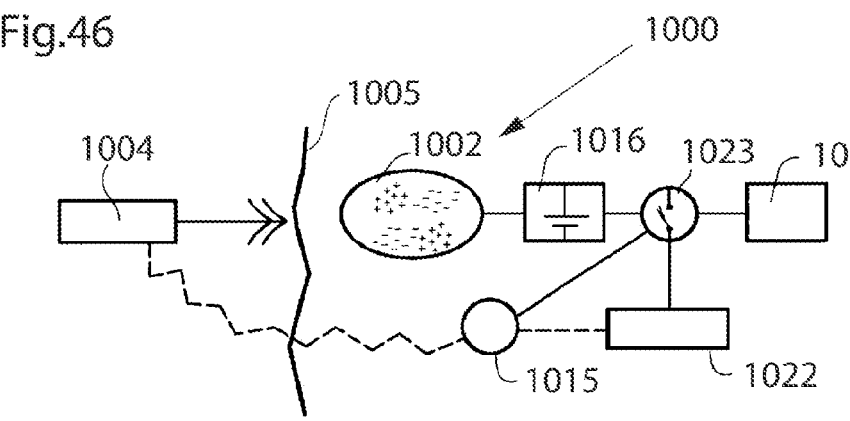
Figure 52:
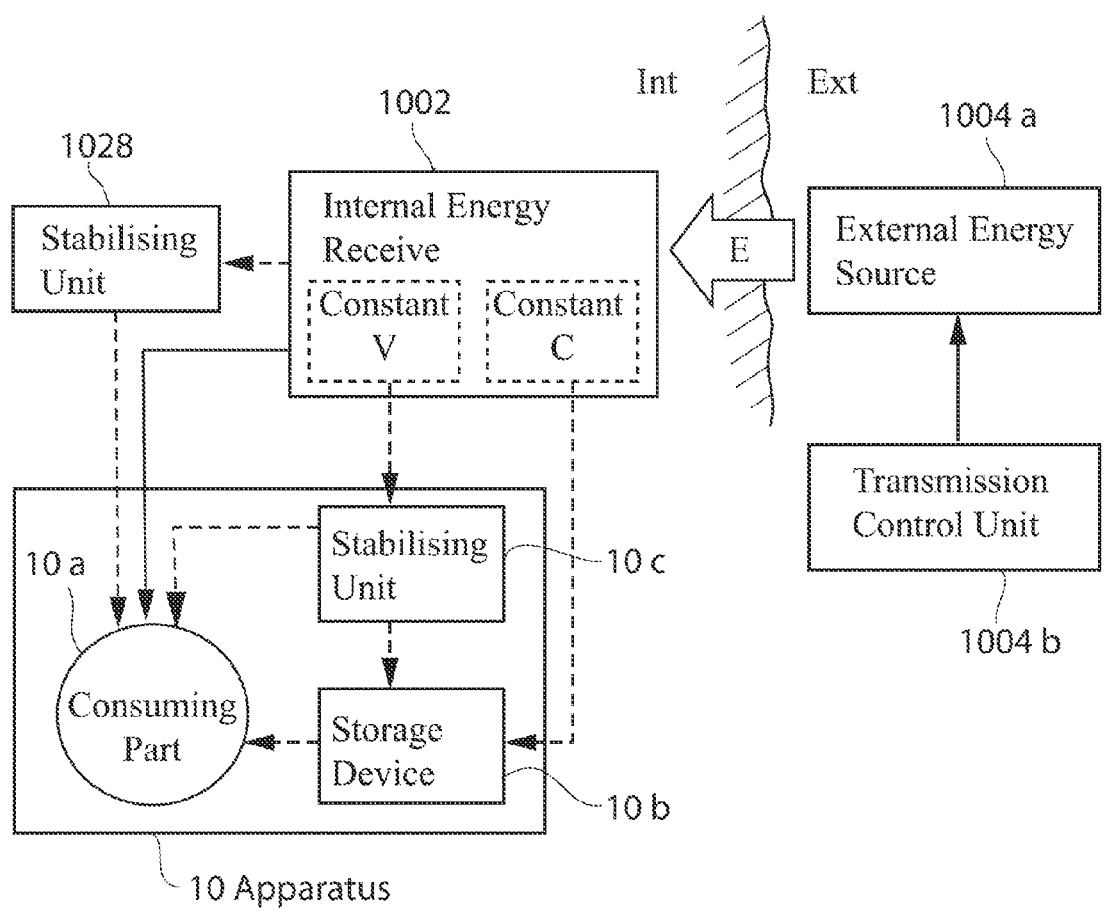
FIG. 52 is a more detailed block diagram of an arrangement for controlling the transmission of wireless energy used for the operation of the apparatus shown in FIG. 34.

FIG. 46 shows an embodiment of the invention identical to that of FIG. 52 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the apparatus 10.

Figure 47:
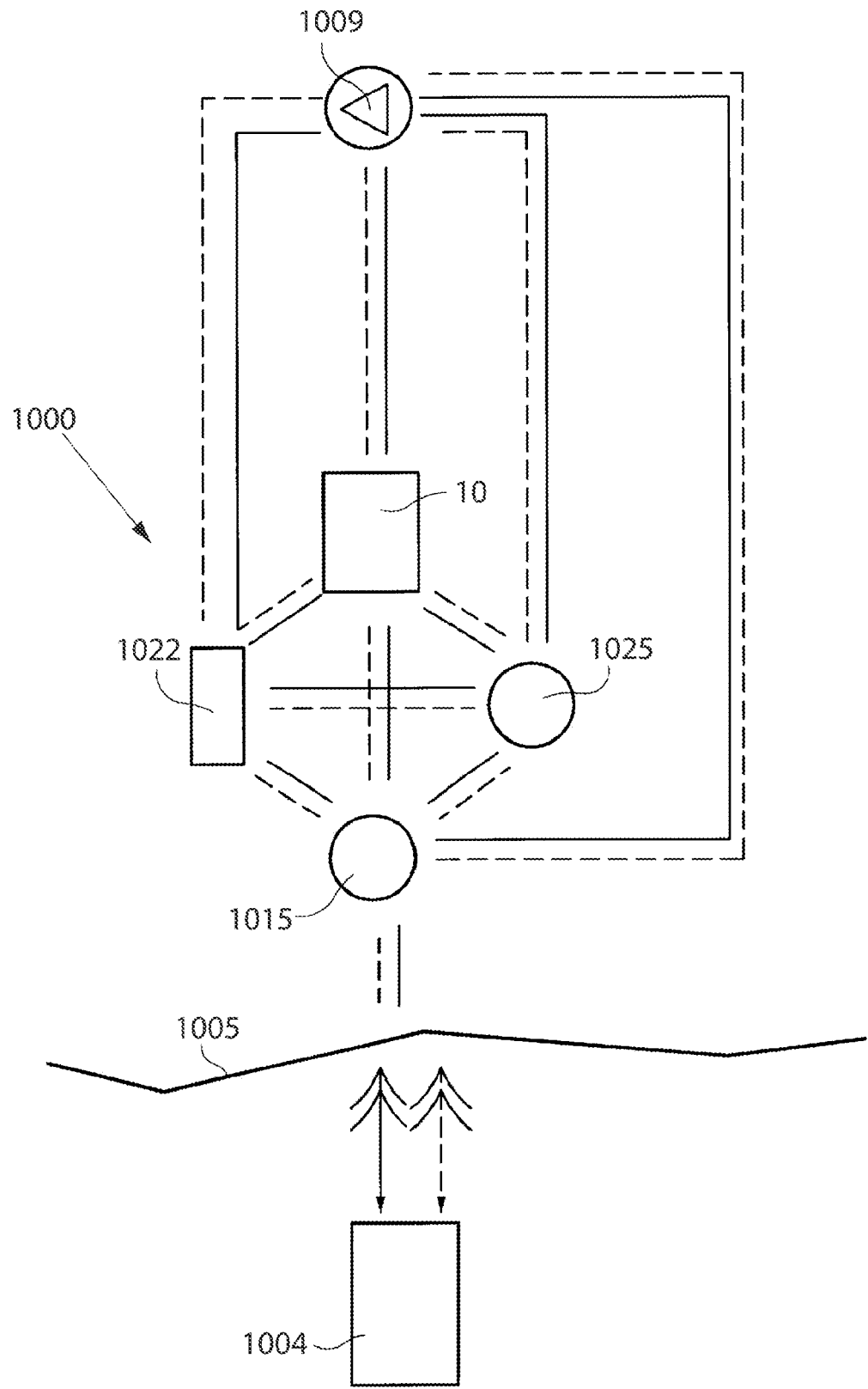

FIG. 47 schematically shows conceivable combinations of implanted components of the apparatus for achieving various communication options. Basically, there are the apparatus 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the apparatus.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the apparatus 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the apparatus 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

Figure 48:
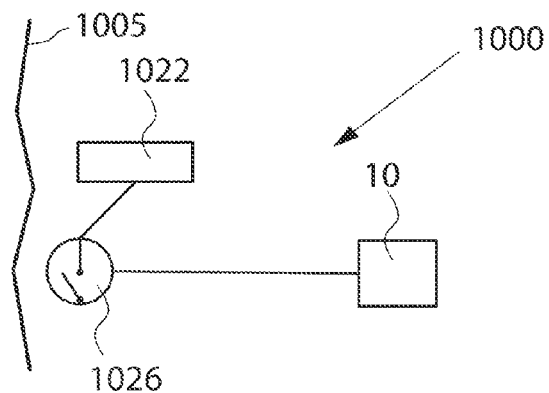

FIG. 48 shows an alternative embodiment wherein the apparatus 10 is regulated from outside the patient's body. The system 1000 comprises a battery 1022 connected to the apparatus 10 via a subcutaneous electric switch 1026. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 49:
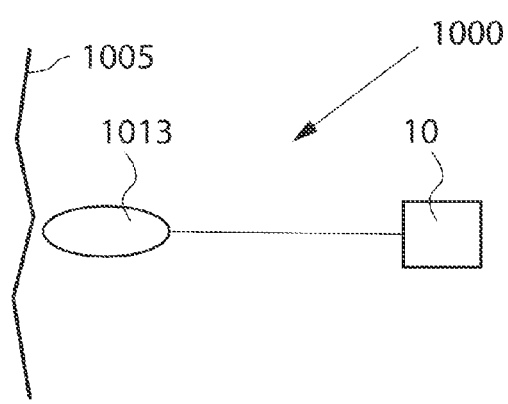

FIG. 49 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus. Alternatively, the hydraulic fluid reservoir 1013 is adapted to work with an injection port for the injection of hydraulic fluid, preferably for calibration of hydraulic fluid.

The system may include an external data communicator and an implantable internal data communicator communicating with the external data communicator. The internal communicator feeds data related to the apparatus or the patient to the external data communicator and/or the external data communicator feeds data to the internal data communicator.

Figure 50:
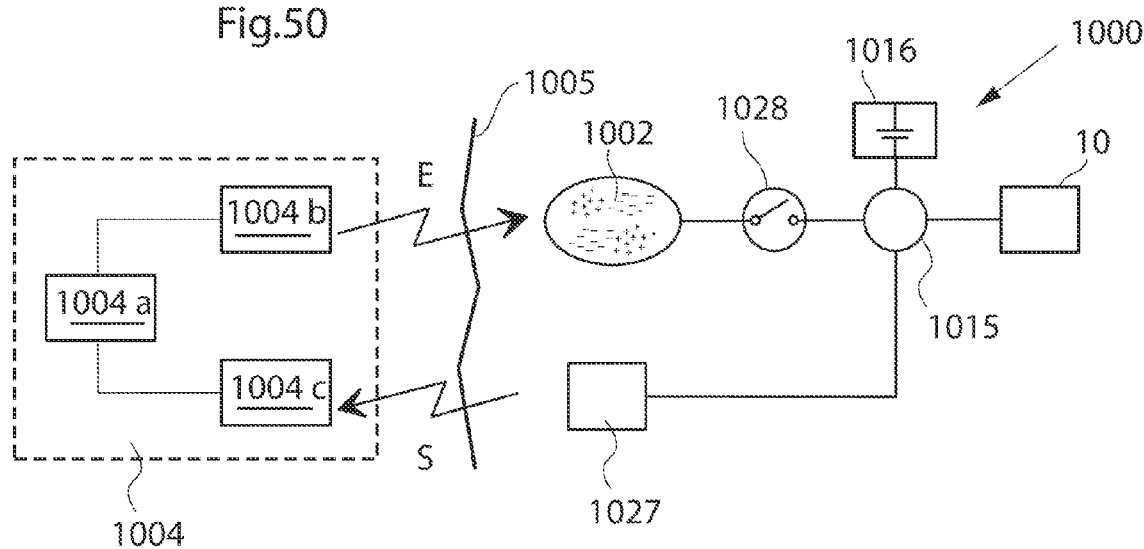
FIG. 50 is a schematic block diagram illustrating an arrangement for supplying an accurate amount of energy used for the operation of the apparatus shown in FIG. 34.

FIG. 50 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 50 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004b based on those sensor measurements.

Hence, the present solution according to the arrangement of FIG. 50 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004c may be implemented as separate units using suitable signal transfer means, such as radio, IR (Infrared) or ultrasonic signals. Alternatively, the internal signal transmitter 1027 and the external signal receiver 1004c may be integrated in the implanted energy-transforming device 1002 and the external energy source 1004a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 50, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 50 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004c. Alternatively, the energy balance can be determined by the external control unit 1004b instead depending on the implementation, as mentioned above. In that case, the control signal may carry measurement results from various sensors. The amount of energy emitted from the external energy source 1004a can then be regulated by the external control unit 1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 51:
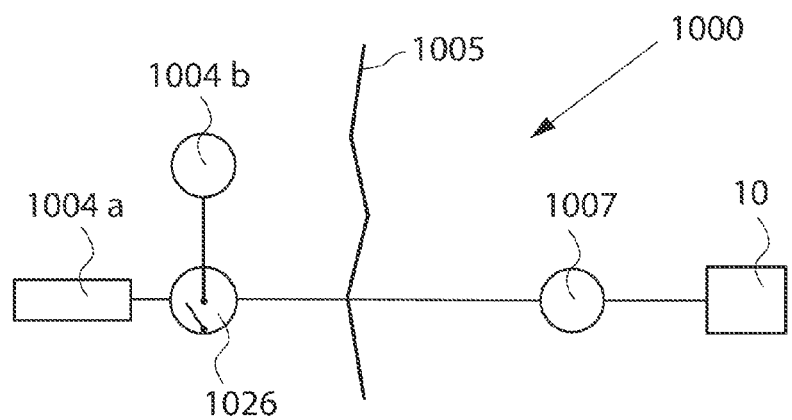
FIG. 51 schematically shows an embodiment of the system, in which the apparatus is operated with wire bound energy.

With reference to FIG. 51, although wireless transfer of energy for operating the apparatus has been described above to enable non-invasive operation, it will be appreciated that the apparatus can be operated with wire bound energy as well. Such an example is shown in FIG. 51, wherein an external switch 1026 is interconnected between the external energy source 1004a and an operation device, such as an electric motor 1007 operating the apparatus 10. An external control unit 1004b controls the operation of the external switch 1026 to effect proper operation of the apparatus 10.

FIG. 52 illustrates different embodiments for how received energy can be supplied to and used by the apparatus 10. Similar to the example of FIG. 50, an internal energy receiver 1002 receives wireless energy E from an external energy source 1004a which is controlled by a transmission control unit 1004b. The internal energy receiver 1002 may comprise a constant voltage circuit, indicated as a dashed box "constant V" in the figure, for supplying energy at constant voltage to the apparatus 10. The internal energy receiver 1002 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 1002. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 10, before being consumed and/or stored by the apparatus 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 50 and FIG. 52 illustrate some possible but non-limiting implementation options regarding how the various shown functional components and elements can be arranged and connected to each other. However, the skilled person will readily appreciate that many variations and modifications can be made within the scope of the present invention.

Figure 53:
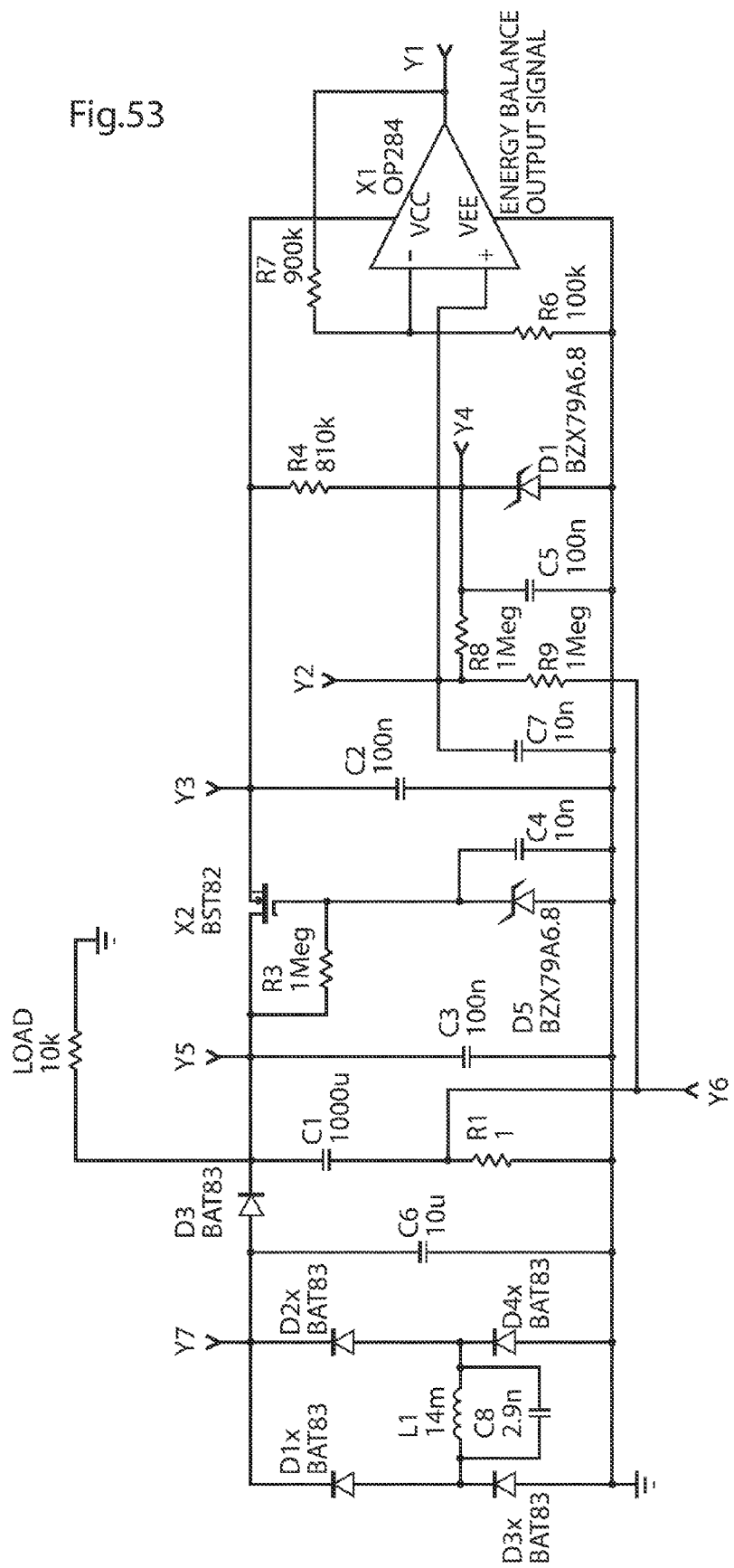
FIG. 53 is a circuit for the arrangement shown in FIG. 52, according to a possible implementation example.

FIG. 53 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 53 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 36; the transmitting parts of the system are excluded.

The implementation of the general concept of energy balance and the way the information is transmitted to the external energy transmitter can of course be implemented in numerous different ways. The schematic FIG. 53 and the above described method of evaluating and transmitting the information should only be regarded as examples of how to implement the control system.

Circuit Details

In FIG. 53 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 36 could be incorporated in any of the embodiments of FIGS. 39-45, the hydraulic valve shifting device 1014 of FIG. 39 could be incorporated in the embodiment of FIG. 38, and the gear box 1024 could be incorporated in the embodiment of FIG. 37. Please observe that the switch simply could mean any electronic circuit or component.

The embodiments described in connection with FIGS. 50, 52 and 53 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

In one embodiment at least one battery may be a part of or replace the energy-transforming device 1002 to supply energy to the apparatus 10 over a power supply line. In one embodiment the battery is not rechargeable. In an alternative embodiment the battery is rechargeable. The battery supply may of course be placed both remote to and incorporated in the device.

Further, the system may comprise any of the following:
- A primary coil in the external energy source adapted to transmit the wireless energy inductively to a secondary coil in the internal energy receiver.
- The determination device is adapted to detect a change in the energy balance, and the control device controls the transmission of wireless energy based on the detected energy balance change
- The determination device is adapted to detect a difference between energy received by the internal energy receiver and energy used for the implantable energy consuming components of the apparatus, and the control device controls the transmission of wireless energy based on the detected energy difference.
- The control device controls the external energy-transmission device to decrease the amount of transmitted wireless energy if the detected energy balance change implies that the energy balance is increasing, or vice versa, wherein the decrease/increase of energy transmission corresponds to a detected change rate.
- The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
- The energy used for the apparatus is consumed to operate the apparatus, and/or stored in at least one energy storage device of the apparatus.
- Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.
- When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.
- When the derivative is determined over time of a measured electrical parameter related to the amount of consumed and/or stored energy, the determination device determines the derivative for a monitored voltage and/or current related to the energy balance.
- The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.
- The electric circuit is adapted to deliver the electrical pulses to remain unchanged except varying the first and/or second time intervals.
- The electric circuit has a time constant and is adapted to vary the first and second time intervals only in the range of the first time constant, so that when the lengths of the first and/or second time intervals are varied, the transmitted power over the coil is varied.
- The electric circuit is adapted to deliver the electrical pulses to be varied by only varying the lengths of first time intervals between successive leading and trailing edges of the electrical pulses.
- The electric circuit is adapted to supplying a train of two or more electrical pulses in a row, said train having a first electrical pulse at the start of the pulse train and having a second electrical pulse at the end of the pulse train, and
- the lengths of the second time intervals between successive trailing edge of the second electrical pulse in a first pulse train and leading edge of the first electrical pulse of a second pulse train are varied by the first electronic circuit.
- The electric circuit is adapted to provide the electrical pulses as pulses having a substantially constant height and/or amplitude and/or intensity and/or voltage and/or current and/or frequency.
- The electric circuit has a time constant, and is adapted to vary the first and second time intervals only in the range of the first time constant, so that when the lengths of the first and/or second time intervals are varied, the transmitted power over the first coil are varied.
- The electric circuit is adapted to provide the electrical pulses varying the lengths of the first and/or the second time intervals only within a range that includes the first time constant or that is located relatively close to the first time constant, compared to the magnitude of the first time constant.

FIGS. 54-57 show in more detail block diagrams of four different ways of hydraulically or pneumatically powering an implanted apparatus according to the invention.

Figure 54:
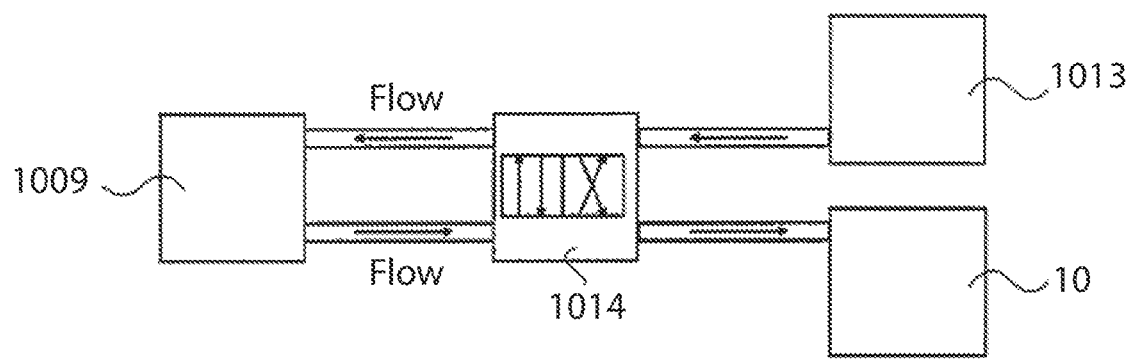
FIGS. 54-60 show various ways of arranging hydraulic or pneumatic powering of an apparatus implanted in a patient.

FIG. 54 shows a system as described above with. The system comprises an implanted apparatus 10 and further a separate regulation reservoir 1013, a one way pump 1009 and an alternate valve 1014.

Figure 55:
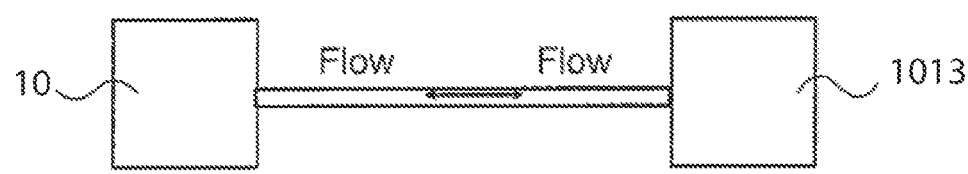

FIG. 55 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 56:
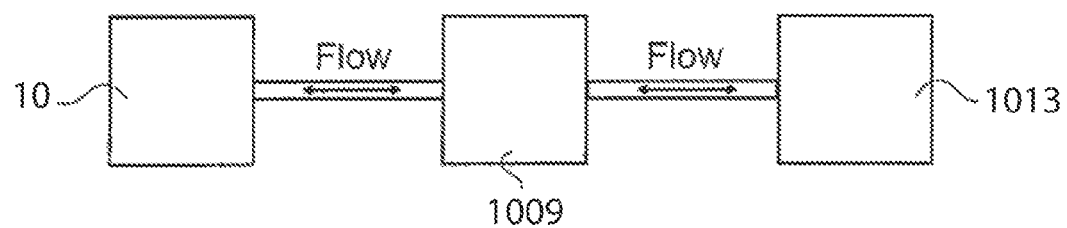

FIG. 56 shows the apparatus 10, a two way pump 1009 and the regulation reservoir 1013.

Figure 57:
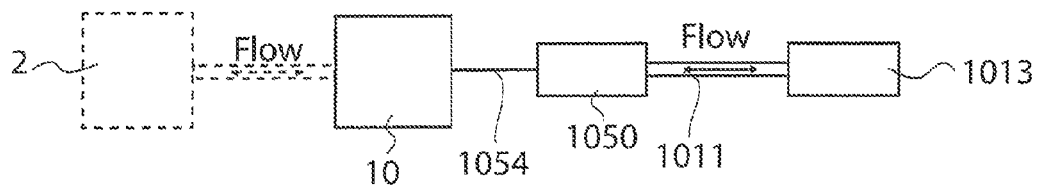

FIG. 57 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

Figure 58A:
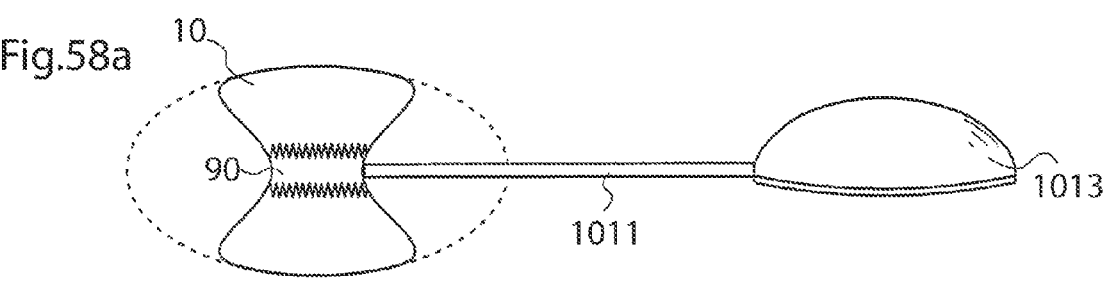
Figure 58B:
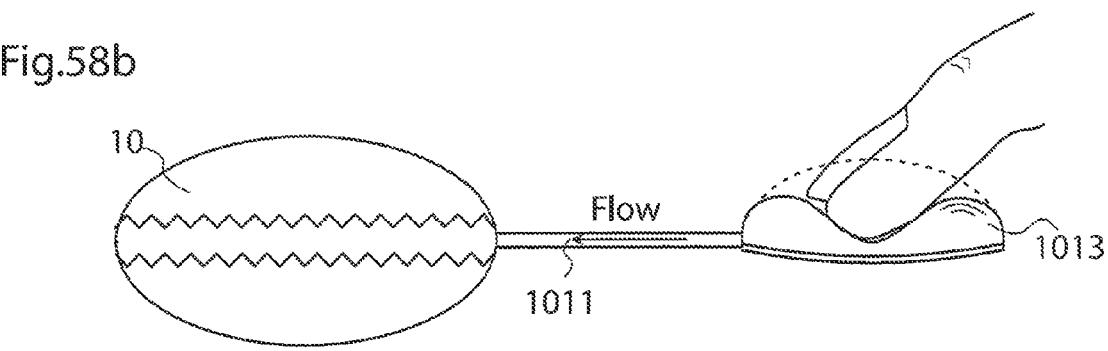
Figure 58C:
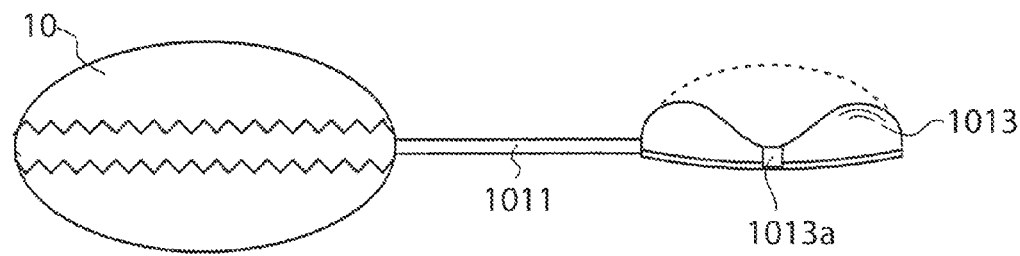
Figure 59:
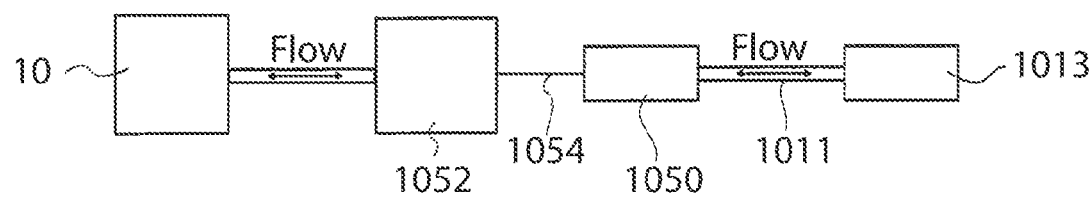

In one embodiment, the regulation reservoir is placed subcutaneous under the patient's skin and is operated by pushing the outer surface thereof by means of a finger. This system is illustrated in FIGS. 58*a-c*. In FIG. 58*a*, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 58*a*, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 58*b* shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 59 and 60*a-c*. The block diagram shown in FIG. 59 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 60A:
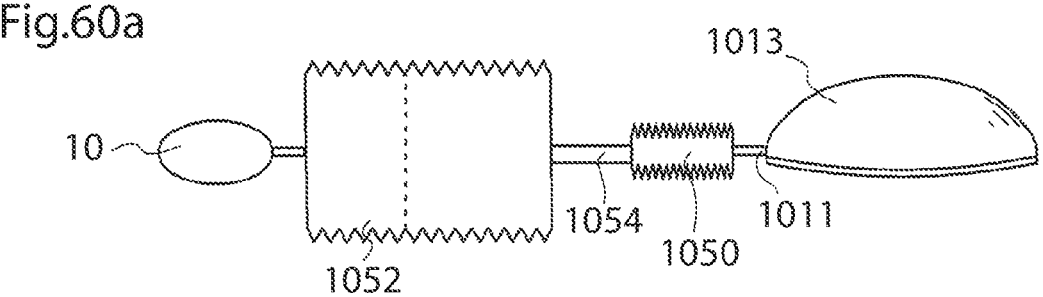
Figure 60B:
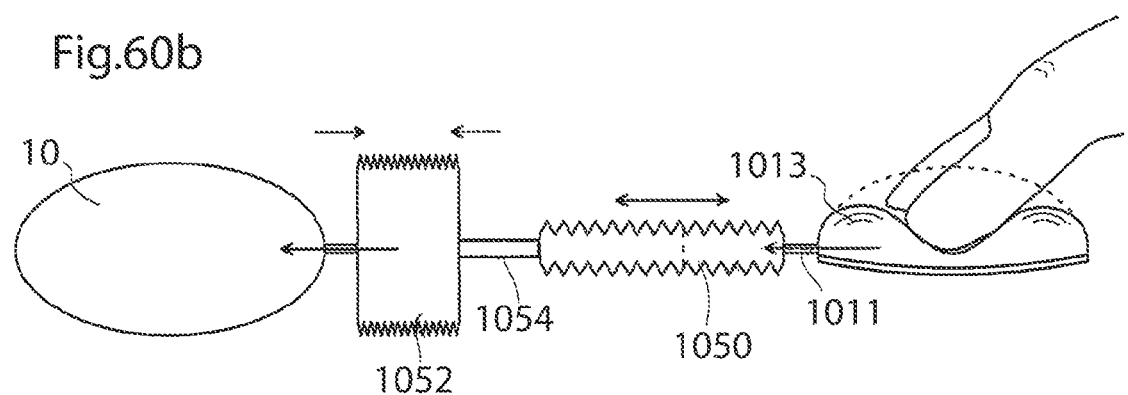
Figure 60C:
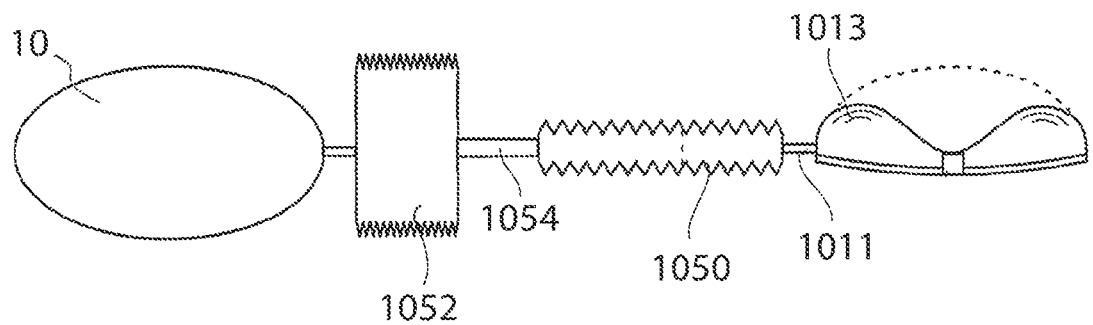

An example of this embodiment will now be described with reference to FIG. 60*a-c*. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 60*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 58*a-c*, the regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Although the different parts described above have specific placements on the drawings it should be understood that these placements might vary, depending on the application.

The lubricating fluid used in any of the embodiments herein is preferably a biocompatible lubricating fluid imitating the synovial fluid of the natural hip joint. According to one embodiment the lubricating fluid is Hyaluronic acid.

In all of the embodiments above it is conceivable that the conduit is excluded and that the channel or channels are in direct connection with the reservoir or the injection port.

Please note that any embodiment or part of embodiment as well as any method or part of method could be combined in any way. All examples herein should be seen as part of the general description and therefor possible to combine in any way in general terms. Please note that the description in general should be seen as describing both of an apparatus and a method.

The various aforementioned features of the invention may be combined in any way if such combination is not clearly contradictory. Individual features of the various embodiments may be combined or exchanged unless such combination or exchange is clearly contradictory to the overall function of the device.

The invention claimed is:

1. An implantable medical device, for implantation in a mammal joint having an acetabulum surface, comprising:
    an artificial concave acetabulum surface, being a bowl shaped surface adapted to replace a surface of the acetabulum surface, wherein said artificial concave acetabulum surface is adapted to be lubricated, when implanted in said joint,
    a reservoir comprising a pumping device and a movable wall portion for changing the volume of the reservoir, for non-invasively transporting a lubricating fluid from said reservoir to said artificial acetabulum surface for lubricating said artificial acetabulum surface,
    at least one inlet adapted to receive said lubricating fluid from the reservoir,
    at least one channel at least partly integrated in said artificial concave acetabulum surface, wherein the channel is in fluid connection with said at least one inlet for distributing said lubricating fluid to the surface of said artificial concave surface,
    an implantable subcutaneous injection port for refilling said reservoir, wherein the movable wall portion is moved when the reservoir is refilled, such that the volume of the reservoir is increased, and wherein the implantable injection port is adapted to allow, by injection into the injection port, preloading of said reservoir with pressurized lubricating fluid, and an interconnecting part for connecting the reservoir and said artificial concave acetabulum surface.

2. The implantable medical device according to claim 1, wherein said at least one channel is adapted to distribute said lubricating fluid to the surface of said artificial concave acetabulum surface on two or more portions of said artificial concave acetabulum surface for lubricating said artificial contacting surface.

3. The implantable medical device according to claim 1, wherein a plurality of channels are at least partly integrated in said artificial concave acetabulum surface.

4. The implantable medical device according to claim 1, wherein said pumping device comprises a pump adapted to pump said lubricating fluid from said reservoir to said artificial concave acetabulum surface for lubricating said artificial acetabulum surface.

5. The implantable medical device according to claim 1, further comprising a valve adapted to close the connection between said reservoir and said artificial surface.

6. The implantable medical device according to claim 1, wherein said reservoir is placed in a unit separate from said artificial surface and adapted to be connected to said artificial surface with a conduit.

7. The implantable medical device according to claim 1, wherein said pumping device comprises a motor.

8. The implantable medical device according to claim 1, wherein said reservoir is adapted to be at least one of:
   at least partly be placed inside of a bone of the patient,
   at least partly be placed inside of the pelvic bone of the patient,
   placed subcutaneously or in a cavity in the body,
   placed in the abdomen, and
   placed subcutaneously or in a cavity in the body in a region of the patient selected from a group of regions consisting of:
      the abdominal region,
      the inguinal region,
      the pelvic region, and
      the thigh region.

9. The implantable medical device according to claim 1, wherein said reservoir is adapted to provide a pressure to said lubricating fluid.

10. The implantable medical device according to claim 9, wherein said reservoir is at least one of:
    spring loaded,
    comprising a chamber adapted to hold a compressed gas, and
    comprising an elastic wall adapted to create said pressure.

11. The implantable medical device according to claim 1, comprising a system for manually and non-invasively controlling the implantable medical device, comprising at least one of; at least one switch implantable in the patient, a wireless remote control, and an implantable hydraulic reservoir which is hydraulically connected to the implantable medical device and adapted to be regulated by manually pressing the hydraulic reservoir.

12. The implantable medical device according to claim 1, comprising a system comprising at least one of;
    an internal energy source for powering implantable energy consuming components of the implantable medical device, and
    an internal energy receiver, and an adaptation to be energized non-invasively and wirelessly by an energy transmission device from outside the patient's body, adapted for sending wireless energy to at least one of:
    an implantable internal energy source comprised in the system, being chargeable by the energy transferred from the energy transmission device, and
    at least one implantable energy consuming component of the system being energized with the wireless energy.

13. The implantable medical device according to claim 1, comprising a system further comprising a sensor and/or a measuring device sensing or measuring at least one of;
    at least one physical parameter of the patient, and
    at least one functional parameter related to the implantable medical device, comprising at least one of a functional parameter correlated to the transfer of energy for charging an internal energy source, and a functional parameter related to the implantable medical device, wherein the implantable medical device further comprising a feedback device for sending feedback information from inside the patient's body to at least one of;
    an implantable internal control unit comprised,
    an external control unit outside of the patient's body,
    an external control unit outside of the patient's body, via the internal control unit,
    an external control unit outside of the patient's body, via the internal control unit according to the programming of the internal control unit performed by the external control unit, wherein the feedback information being related to at least one of; the at least one physical parameter of the patient and the at least one functional parameter related to the implantable medical device.

14. The implantable medical device according to claim 1, wherein said reservoir is a pre-pressurized reservoir, adapted to move said lubricating fluid from said pre-pressurized reservoir to said artificial concave acetabulum surface for lubricating said artificial acetabulum surface.

* * * * *